United States Patent
Raubitschek et al.

(10) Patent No.: US 6,410,319 B1
(45) Date of Patent: Jun. 25, 2002

(54) CD20-SPECIFIC REDIRECTED T CELLS AND THEIR USE IN CELLULAR IMMUNOTHERAPY OF CD20+ MALIGNANCIES

(75) Inventors: Andrew Raubitschek, San Marino; Anna Wu, Sherman Oaks; Michael C. Jensen, Pasadena, all of CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/421,295

(22) Filed: Oct. 20, 1999

Related U.S. Application Data
(60) Provisional application No. 60/105,014, filed on Oct. 20, 1998.

(51) Int. Cl.[7] .......................... C12N 5/06; C12N 15/00; C12N 5/00; C12N 5/08; C07H 21/04

(52) U.S. Cl. ................................ 435/343.1; 435/320.1; 435/325; 435/326; 435/328; 435/332; 435/343; 435/344; 435/372; 435/372.2; 435/372.3; 536/23.1; 536/23.4

(58) Field of Search .............................. 435/372, 347.2, 435/375, 69.1, 320.1, 455, 325, 326, 328, 332, 343, 343.1, 344; 536/23.4

(56) References Cited

U.S. PATENT DOCUMENTS

| | | | |
|---|---|---|---|
| 5,359,046 A | 10/1994 | Capon et al. ............... 536/23.4 |
| 5,712,149 A | * | 1/1998 | Roberts .................... 435/252.3 |

FOREIGN PATENT DOCUMENTS

| | | |
|---|---|---|
| WO | WO 94 11026 A | 5/1994 |
| WO | WO 97 23613 A | 7/1997 |
| WO | WO 98 41613 A | 9/1998 |

OTHER PUBLICATIONS

M Jensen et al., Biology of Blood and Marrow Transplantation, "CD20 is a Molecular target for scFvFc:Zeta receptor redirected T cells:implications for cellular immunotherapy of CD20= malignancy," Aug. 1998, 4:75–83.*

M. Jensen et al., "CD20 is a molecular target for scFvFc:ζ receptor redirected T cells: implications for cellular immunotherapy of CD20+ malignancy," *Biology of Blood and Marrow Transplantation*, vol. 4, No. 2, 1998, pp. 75–83.

H. Abken et al., "Can combined T–cell– and antibody–based immunotherapy outsmart tumor cells?" *Immunology Today*, vol. 19, No. 1, Jan. 1998, pp. 1–5.

H. Haisma et al., "Construction and characterization of a fusion protein of single–chain anti–CD20 antibody and human beta–glucuronidase for antibody–directed enzyme prodrug therapy," *Blood*, vol. 92, No. 1, Jul. 1, 1998, pp. 184–190.

(List continued on next page.)

Primary Examiner—James Ketter
Assistant Examiner—Q. Janice Li
(74) Attorney, Agent, or Firm—Rothwell, Figg, Ernst & Manbeck

(57) ABSTRACT

Genetically engineered, CD20-specific redirected T cells expressing a cell surface protein-having an extracellular domain comprising a receptor which is specific for CD20, an intracellular signaling domain, and a transmembrane domain. Use of such cells for cellular immunotherapy of CD20+ malignancies and for abrogating any untoward B cell function. In one embodiment, the cell surface protein is a single chain FvFc:ζ receptor where Fv designates the $V_H$ and $V_L$ chains of a single chain monoclonal antibody to CD20 linked by peptide, Fc represents a hinge-$CH_2$–$CH_3$ region of a human $IgG_1$, and ζ represents the intracellular signaling domain of the zeta chain of human CD3. A method of making a redirected T cell expressing a chimeric T cell receptor by electroporation using naked DNA encoding the receptor.

22 Claims, 3 Drawing Sheets

OTHER PUBLICATIONS

D. Anderson et al., "Targeted anti–cancer therapy using rituximab, a chimaeric anti–CD20 antibody (IDEC–C2B8) in the treatment of non–Hodgkin's B–cell lymphoma," *Biochemical Society Transactions*, vol. 25, 1997, pp. 705–708.

M. Jensen et al., "Specific recognition and lysis of CD20+ lymphoma cells by primary human CD8+ CTL clones genetically modified to express a CD20–specific chimeric immunoreceptor," *Blood*, vol. 92, No. 10, suppl. 1 (part 1 of 2), Nov. 15, 1998, p. 245a. (Abstract #998).

Shipp, M. A., et al., "Non–Hodgkin's Lymphomas", Cancer: Principles and Practice of Oncology, Lippincott–Raven Publishers, Philadelphia, 1997, pp. 2165–2220.

Glass, A. G., et al., "The National Cancer Data Base Report on Non–Hodgkin's Lymphoma", Cancer, vol. 80, No. 12, 1997, pp. 2311–2320.

Heslop, H. E., et al., "Adoptive Cellular Immunotherapy for EBV Lymphoproliferative Diseases", Immunol. Rev., vol. 157, 1997, pp. 217–222.

Gross, G., et al., "Endowing T Cells With Antibody Specificity Using Chimeric T Cell Receptors," FASEB J., vol. 6, 1992, pp. 3370–3378.

Eshhar, Z., et al., "Specific Activation and Targeting of Cytotoxic Lymphocytes Through Chimeric Single Chains Consisting of Antibody–Binding Domains and the γ or ζ Subunits of the Immunoglobulin and T–cell Receptors," PNAS USA, vol. 90, 1993, pp. 720–724.

Stancovski, I., et al., "Targeting of T Lymphocytes to Neu/HER2–Expressing Cells Using Chimeric Single Chain Fv Receptors," J. Immunol., vol. 151, 1993, pp. 6377–6382.

Moritz, D., et al., "Cytotoxic T Lymphocytes with a Grafted Recognition Specificity for ERBB2–Expressing Tumor Cells," PNAS USA, vol. 91, 1994, pp. 4318–4322.

Hwu, P., et al., "In Vivo Antitumor Activity of T Cells Redirected with Chimeric Antibody/T–Cell Receptor Genes," Cancer Res., vol. 55, 1995, pp. 3369–3373.

Hwu, P., et al., "The Genetic Modification of T Cells for Cancer Therapy: An Overview of Laboratory and Clinical Trials," Cancer Detection and Prevention, vol. 18, No. 1, 1994, pp. 43–50.

Weitjens, M. E. M., et al., "Single Chain Ig/γ Gene–Redirected Human T Lymphocytes Produce Cytokines, Specifically Lyse Tumor Cells, and Recycle Lytic Capacity," J. Immunol., vol. 157, 1996, pp. 836–843.

Hekele, A., et al., "Growth Retardation of Tumors by Adoptive Transfer of Cytotoxic T Lymphocytes Reprogrammed by CD44V6–Specific SCFV:ζ–Chimera," Int. J. Cancer, vol. 68, 1996, pp. 232–238.

Vervoordeldonk, S. F., et al., "Preclinical Studies with Radiolabeled Monoclonal Antibodies for Treatment of Patients with B–Cell Malignancies," Cancer, vol. 73, 1994, pp. 1006–1011.

Press, O. W., et al., "Retention of B–Cell–Specific Monoclonal Antibodies by Human Lymphoma Cells," Blood, vol. 83, 1994, pp. 1390–1397.

Bubien, J. K., et al., "Transfection of the CD20 Cell Surface Molecule into Ectopic Cell Types Generates a Ca2+ Conductance Found Constitutively in B Lymphocytes," J. Cell Biol., vol. 121, 1993, pp. 1121–1132.

Henkart, P.A., "Introduction: CTL Effector Functions", Semin. Immunol., vol. 9, 1997, pp. 85–86.

Greenberg, P. D., et al., "Genetic Modification of T–Cell Clones for Therapy of Human Viral and Malignant Diseases," The Cancer Journal from Scientific American, vol. 4, 1998, pp. S100–105.

Greenberg, P. D., "Adoptive T Cell Therapy of Tumors: Mechanism Operative in the Recognition and Elimination of Tumor Cells," Adv. Immunol., vol. 49, 1991, pp. 281–355.

Robbins, P. F., et al., "Human Tumor Antigens Recognized by T Cells," Current Opin. Immunol., vol. 8, 1996, pp. 628–636.

De Plaen, E., et al., "Identification of Genes Coding for Tumor Antigens Recognized by Cytolytic T Lymphocytes," Methods, vol. 12, 1997, pp. 125–142.

Yee, C., et al., "Isolation of Tyrosinase–Specific CD8+ and CD4+ T Cell Clones From the Peripheral Blood of Melanoma Patients Following in Vitro Stimulation with Recombinant Vaccinia Virus," J. Immunol., vol. 157, 1996, pp. 4079–4086.

Weiss, A., et al., "Signal Transduction by the T Cell Antigen Receptor," Semin. Immunol., vol. 3, 1991, pp. 313–324.

Hedrick, S. M., et al., "Chimeric T Cell Receptor–Immunoglobulin Molecules: Function and Applications," Int. Rev. Immunol., vol. 10, 1993, pp. 279–290.

Fitzer–Attas, C. J., et al., "Harnessing Syk Family Tyrosine Kinases as Signaling Domains for Chimeric Single Chain of the Variable Domain Receptors: Optimal Design for T Cell Activation," J. Immunol., vol. 160, 1998, pp. 145–154.

Eshhar, Z., "Tumor–specific T–bodies: Towards Clinical Application", Cancer Immunol. Immunother., vol. 45, 1997, pp. 131–136.

Altenschmidt, U., et al., "Specific Cytotoxic T Lymphocytes in Gene Therapy," J. Mol. Med., vol. 75, 1997, pp. 259–266.

Brocker, T., et al., "Adoptive Tumor Immunity Mediated by Lymphocytes Bearing Modified Antigen–Specific Receptors," Adv. Immunol., vol. 68, 1998, pp. 257–269.

Rosenberg, et al., "Human Gene Marker/Therapy Clinical Protocols," Human Gene Therapy, vol. 8, 1997, pp. 2301–2338.

Ebert, O., et al., "Lymphocyte Apoptosis: Induction by Gene Transfer Techniques," Gene Ther., vol. 4, 1997, pp. 296–302.

Gallot, G., et al., "Human HLA–Specific T–Cell Clones With Stable Expression of a Suicide Gene: A Possible Tool to Drive and Control a Graft–Versus–Host–Graft–Versus–Leukemia Reaction?", Blood, vol. 88, 1996, pp. 1098–1103.

Roberts, M. R., et al., "Targeting of Human Immunodeficiency Virus–Infeced Cells by CD8+ T Lymphocytes Armed With Universal T–Cell Receptors," Blood, vol. 84, 1994, pp. 2878–2889.

Hege, K. M., et al., "T–Cell Gene Therapy," Current Opinion in Biotechnology, vol. 7, 1996, p. 629–634.

Kozak, Nucl. Acids Res. 15:8125, 1987.

Neumaier, Cancer Res. 50:2128, 1990.

"CD20 (Leu™–16)," Monoclonal Antibodies Detecting Human Antigens, Becton Dickinson Immunocytometry Systems, Becton Dickinson, San Jose, California.

Dübel, S., et al., Isolation of IgG Antibody Fv–DNA from Various Mouse and Rat Hybridoma Cell Lines Using the Polymerase Chain Reaction with a Simple Set of Primers, J.Immunol. Meth., vol. 175, 1994, pp. 89–95.

Honjo, T., et al., "Cloning and Complete Nucleotide Sequence of Mouse Immunoglobulin Chain Gene", Cell, vol. 18, 1979, pp. 559–568.

Heiter, P. A., et al., "Cloned Human and Mouse Kappa Immunoglobulin Constant and J Region Genes Conserve Homology in Functional Segments," Cell, vol. 22, 1980, pp. 197–207.

Weissman, A. M., et al., "Molecular Cloning and Chromosomal Localization of the Human T–Cell Receptor Zeta Chain: Distinction From the Molecular CD3 Complex," Proc. Nat. Acad. Sci., vol. 85, 1988, pp. 9709–9713 (Abstract).

Weissman, A. M., "Molecular Cloning of the Zeta Chain of the T Cell Antigen Receptor," Science, vol. 239, 1988, pp. 1018–1021.

Moingeon, P., et al., "Human Natural Killer Cells and Mature T–Lymphocytes Express Identical CD3 Zeta Subunits as Defined by cDNA Cloning and Sequence Analysis," Eur. J. Immunol., vol. 20, 1990, pp. 1741–1745 (Abstract).

Kranz, D. M., et al., "Attachment of an Anti–Receptor Antibody to Non–target Cells Renders Them Susceptible to Lysis by a Clone of Cytotoxic T Lymphocytes," Proc. Natl. Acad. Sci. USA, vol. 81, 1984, pp. 7922–7926.

Pelloquin, F., et al., "Human B Lymphocytes Immortalization by Epstein–Barr Virus in the Presence of Cyclosporin A," in Vitro Cell Dev. Biol., vol. 22, 1986, pp. 689–694.

Sambrook, J., et al., "Isolation of DNA from Mammalian Cells: protocol I," Molecular Cloning, 2d Ed., 1989, pp. 9.16–9.19.

Jensen, J. P., et al., "Organization of the Human T Cell Receptor $\zeta/\eta$ Gene and Its Genetic Linkage to the Fc$\gamma$RII–Fc$\gamma$RIII Gene Cluster," J. Immunol., vol. 148, 1992, pp. 2563–2571.

Riddell, S. R., et al., "Restoration of Viral Immunity in Immunodeficient Humans by the Adoptive Transfer of T Cell Clones," Science, vol. 257, 1992, pp. 238–241.

Walter, E. A., et al., "Reconstitution of Cellular Immunity Against Cytomegalovirus in Recipients of Allogeneic Bone Marrow by Transfer of T–Cell Clones From the Donor," N. Engl. J. Med., vol. 333(16), 1995, pp. 1038–1044.

Heslop, H. E., et al., "Long–term Restoration of Immunity Against Epstein–Barr Virus Infection by Adoptive Transfer of Gene–Modified Virus–Specific T Lymphocytes," Nat. Med., vol. 2, 1996, pp. 551–555.

Rosenberg, S. A., et al., "Prospective Randomized Trial of High–Dose Interleukin–2 Alone or in Conjuction With Lymphokine–Activated Killer Cells for the Treatment of Patients With Advanced Cancer," J. Natl. Cancer Inst, vol. 85, 1993, pp. 622–632 and 1091, 1993.

Rosenberg, S. A., et. al., "Use of Tumor–Infiltrating Lymphocytes and Interleukin–2 in the Immunotherapy of Patients With Metastatic Melanoma," N. Engl. J. Med., vol. 319, 1988, pp. 1676–1680.

van Pel, A., et al., "Genes Coding for Tumor Antigens Recognized by Cytolytic T Lymphocytes," Immunol. Rev., vol. 145, 1995, pp. 229–250.

Porter, D. L., et al., "Graft–Versus–Leukemia Effect of Allogeneic Bone Marrow Transplantation and Donor Mononuclear Cell Infusions," Cancer Treat Res., vol. 77, 1997, pp. 57–85.

van Lochem, E., et al., "In Vitro Separation of Host Specific Graft–Versus–Host and Graft–Versus–Leukemia Cytotoxic T Cell Activities," Bone Marrow Transplant., vol. 10, 1992, pp. 181–183.

Cardoso, A. A., et al., "Ex Vivo Generation of Human Anti–Pre–B Leukemia–Specific Autologous Cytolytic T Cells," Blood, vol. 90, 1997, pp. 549–561.

Dolstra, H., et al., "Recognition of a B Cell Leukemia–Associated Minor Histocompatibility Antigen by CTL," J. Immunol., vol. 158, 1997, pp. 560–565.

Dohi, Y., et al., "Successful Generation of Cytotoxic T Lymphocytes Specific for Self Immunoglobulin–Determinants on B Lymphocytes," J. Immunol., vol. 135, 1985, pp. 47–52.

Chakrabarti, D., et al., "Induction of Syngeneic Cytotoxic T Lymphocytes Against a B Cell Tumor," Cell Immunol., vol. 144, 1992, pp. 455–464.

Irving, B. A., et al., "The Cytoplasmic Domain of the T Cell Receptor $\zeta$ Chain is Sufficient to Couple to Receptor–Associated Signal Transduction Pathways," Cell, vol. 64, 1991, pp. 891–901.

Bird, A. G., et al., "Cyclosporin A Promotes Spontaneous Outgrowth in Vitro of Epstein–Barr Virus–Induced B–Cell Lines," Nature, vol. 289, 1981, p. 300–301.

Bird, A. G., et al., "Single–Chain Antigen–Binding Proteins," Science, vol. 242, 1988, pp. 423–426.

Gross, G., et al., "Chimaeric T–Cell Receptors Specific to a B–Lymphoma Idotype: a Model for Tumour Immunotherapy," Biochem. Soc. Trans., vol. 23, 1995, pp. 1079–1082.

Glimcher, L. H., et al., "Ia Antigen–Bearing B Cell Tumor Lines Can Present Protein Antigen and Alloantigen in a Major Histocompatibility Complex–Restricted Fashion to Antigen–Reactive T Cells," Journal of Experimental Medicine, vol. 155, 1982, pp. 445–459.

Dorfman, D. M., et al., "In Vivo Expression of B7–1 and B7–2 by Follicular Lymphoma Cells Can Prevent Induction of T–Cell Anergy But is Insufficient to Induce Significant T–Cell Proliferation," Blood, vol. 90(11), 1997, pp. 4297–4306.

Daniel, P., T., et al., "Costimulatory Signals Through B7.1/ CD28 Prevent T Cell Apoptosis During Target Cell Lysis," J. Immunol., vol. 159, 1997, pp. 3808–3815.

Chao, C., et al., "Mechanisms of L–Selectin Regulation by Activated T Cells," J. Immunol., vol. 159, 1997, pp. 1686–1694.

Tedder, T. F., et al., "CD20:a Regulatory of Cell–Cycle Progression of B Lymphocytes," Immunnol. Today, vol. 15(9), 1994, pp. 450–454.

Shan, D., et al., "Apoptosis of Malignant Human B Cells by Ligation of CD20 With Monoclonal Antibodies," Blood, vol. 91, 1998, pp. 1644–1652.

Ghetie, M., et al., "Homodimerization of Tumor–Reactive Monoclonal Antibodies Markedly Increases Their Ability to Induce Growth Arrest or Apoptosis of Tumor Cells," PNAS USA, vol. 94, 1997, pp. 7509–7514.

Maloney, D. G., et al., "IDEC–C2B8 (Rituximab) Anti–CD20 Monoclonal Antibody Therapy in Patients With Relapsed Low–Grade Non–Hodgkin's Lymphoma," Blood, vol. 90, 1997, pp. 2188–2195.

Eary, J. F., et al., "High Dose Radioimmunotherapy in Malignant Lymphoma," Recent Result Cancer Res., vol. 141, 1996, pp. 177–181.

Bonini, C., et al., "HSV–TK Gene Transfer into Donor Lymphocytes for Control of Allogeneic Graft–Versus–Leukemia," Science, vol. 276, 1997, pp. 1719–1724.

\* cited by examiner

CD20-SPECIFIC REDIRECTED T CELLS AND THEIR USE IN CELLULAR IMMUNOTHERAPY OF CD20+ MALIGNANCIES

CROSS-REFERENCE TO RELATED APPLICATION

Applicants claim the benefit of U.S. Provisional Application Serial No. 60/105,014 filed Oct. 20, 1998, now abandoned.

This invention was made during research funded in part by United States National Cancer Institute Grant No. 30206. The U.S. Government may have certain rights in the invention.

BACKGROUND OF THE INVENTION

1. Technical Field

This invention relates to the field of genetically engineered, redirected T cells and to the field of cellular immunotherapy of malignancies such as Non-Hodgkin's lymphoma and lymphocytic leukemia.

2. Description of Related Art

Over 30,000 new cases of Non-Hodgkin's lymphoma are diagnosed each year in the United States alone. (Shipp et al., Cancer: *Principles and Practice of Oncology*, Lippincott-Raven Publishers, Philadelphia, 1997, p2165). While current therapies have produced significant complete response rates, a large percentage of patients remain at significant risk for disease relapse (Glass et al., *Cancer* 80:2311, 1997). Immune-based strategies for targeting minimal residual disease are under development and may provide additional modalities for consolidating standard chemotherapy and radiotherapy regimens. The approach of treating lymphoma with adoptive T cell therapy is predicated on the assumptions that tumor-reactive T cells can be isolated from individuals with lymphoma and expanded in vitro, and that infusion of the expanded effector population into the patient will mediate an antitumor effect without significant toxicity. Adoptively transferred donor-derived Epstein-Barr virus (EBV)-specific T cells can eliminate transformed B cells as demonstrated in the setting of post-transplant EBV-associated lymphoproliferative disease (Heslop et al., *Immunol. Rev.* 157:217, 1997). The clinical application of cellular immunotherapy for lymphoma using autologous T cells is currently limited by the paucity of molecularly-defined lymphoma target antigens for T cell recognition and the challenges of reliably isolating and expanding tumor-antigen specific T cell responses from cancer patients.

In order to overcome these obstacles, we and others are evaluating chimeric antigen receptor constructs consisting of a monoclonal antibody single chain Fv (scFv) linked to the intracellular signaling domain of CD3 zeta or FcγRIII for the purpose of re-directing T cell specificity. This strategy allows for the targeting of tumor cells based on the binding of the scFv portion of the receptor to monoclonal antibody-defined cell-surface epitopes. The capacity of these receptors when expressed in T cells to trigger cytokine production and cytolysis in vitro is now well established in both murine and human T cells. See Gross et al., *FASEB J.* 6:3370, 1992; Eshhar et al., *PNAS USA*, 90:720, 1993; Stancovski et al., *J. Immunol.*, 151:6577, 1993; Moritz et al., *PNAS USA* 91:4318, 1994; Hwu et al., *Cancer Res.*, 55:3369, 1995; Weitjens et al., *J. Immunol.* 157:836, 1996. Animal model systems demonstrate the capacity of murine T cell transfectants to eradicate tumor in vivo, suggesting that these gene-modified cells retain appropriate homing and recycling mechanisms (Hekele et al., *Int. J. Cancer* 68:232, 1996). This system is not dependent on pre-existing antitumor immunity since the generation of tumor-reactive T cells for therapy can be accomplished by the genetic modification of polyclonal T cells present in peripheral blood. Moreover, target epitope recognition by scFv is not HLA-restricted, thereby permitting the use of receptor constructs in populations of lymphoma patients irrespective of HLA differences.

A critical aspect of this chimeric receptor strategy is the selection of target epitopes that are specifically or selectively expressed on tumor, are present on all tumor cells, and are membrane epitopes not prone to shed or modulate from the cell surface. Nearly 80% of Non-Hodgkin's lymphoma are B cell in origin and are defined in part by the cell surface expression of the CD20 molecule. This 33–37 KD protein is uniformly expressed on normal B cells and malignant B cells at a density greater than 12,000 molecules per cell (Vervoordeldonk et al., *Cancer* 73:1006, 1994). CD20 does not modulate or shed from the cell surface and has structural features consistent with that of an ion channel (Press et al., *Blood* 83:1390, 1994; Bubien et al., *J. Cell Biol.* 121:1121, 1993). The United States Food and Drug Administration (FDA) has approved a chimeric CD20-specific monoclonal antibody (rituximab) for lymphoma therapy. Initial clinical experience with CD20-targeted immunotherapy suggests that malignant B cells may have a limited capacity to down regulate CD20 expression. These attributes make CD20 an attractive target for genetically engineered, redirected T cells.

$CD8^+$ cytolytic T cells (CTL) are immunologic effector cells that have the capacity to specifically recognize and directly lyse target cells (Henckart, *Semin. Immunol.* 9:85, 1997). Re-infusion of ex vivo expanded tumor-specific $CD8^+$ CTL clones can mediate tumor eradication as demonstrated in animal model systems (Greenberg, *Adv. Immunol.* 49:281,1991). A growing number of genes encoding proteins expressed by human tumors that elicit T cell responses have been identified by expression cloning technologies. (Robbins et al., *Current Opin. Immunol.* 8:628, 1996; De Plaen et al., *Methods* 12:125, 1997). The feasibility of isolating T cells from cancer patients with specificity for these molecularly defined tumor antigens is currently being evaluated but remains a significant challenge to the clinical application of adoptive T cell therapy for malignant disease (Yee et al., *J. Immunol.* 157:4079, 1996).

Endowing T cells with tumor specificity by gene transfer of cDNA constructs encoding engineered antigen receptors is an alternate strategy for generating tumor-reactive CTL for therapy. (Weiss et al., *Semin. Immunol.* 3:313, 1991; Gross et al., supra; Hedrick et al., *Int. Rev. Immunol.* 10:279, 1993). These cell-surface chimeric molecules are distinguished by their ability to both bind antigen and transduce activation signals via immunoreceptor tyrosine-based activation motifs (ITAM's) present in their cytoplasmic tails. Receptor constructs utilizing an antigen-binding moiety generated from single chain antibodies (scFv) afford the additional advantage of being "universal" in that they bind native antigen on the target cell surface in an HLA class I independent fashion. Several laboratories have reported on scFv constructs fused to sequences coding for the intracellular portion of the CD3 complex's zeta chain (ζ), the Fc receptor gamma chain, and sky tyrosine kinase (Eshhar et al., supra; Fitzer-Attas et al., *J. Immunol.* 160:145, 1998). Re-directed T cell effector mechanisms including tumor recognition and lysis by CTL have been documented in several murine and human antigen-scFv:ζ systems (Eshhar, *Cancer Immunol. Immunother.* 45:131, 1997; Altenschmidt et al., *J. Mol. Med.* 75:259, 1997; Brocker et al., *Adv. Immunol.* 68:257, 1998.

Clinical cellular immunotherapy trials have utilized gene-modified T cells for gene marking purposes, the expression of suicide genes permitting in vivo ablation of transfected cells, the expression of genes designed to protect T cells from HIV infection, and the expression of chimeric antigen receptors (Rosenberg et al., *Human Gene Therapy* 8:2301, 1997). A growing number of applications of T cell gene therapy for manipulating T cell survival, trafficking, and effector functions are under development for clinical application. To date, retroviral vectors remain the preeminent modality for gene transfer into primary human T cells. These vectors provide for relatively high transduction efficiencies and stable chromosomal integration but place constraints on the sequence and amount of cDNA which can be packaged and are difficult, time consuming, and expensive to produce as clinical grade material. A gene transfer system that provides a high degree of flexibility with respect to the configuration and sequence of cDNA constructs, that can be rapidly modified, and that is non-infectious and inexpensive to produce as a clinical reagent, may provide a viable alternative to retroviral systems.

Plasmid DNA represents a highly versatile platform for constructing expression cassettes that are active in mammalian cells. When combined with electroporation, a procedure by which DNA is introduced into cells through transient pores formed in the plasma membrane following exposure to brief electrical current, a simple and easily applied gene transfer system is created. Although transformed human lymphoid cell lines are amenable to stable transfection by electroporation of plasmid vectors, primary human T cells have been regarded to be resistant to this methodology for stable modification (Ebert et al., *Gene Ther.* 4: 296, 1997; Gallot et al., *Blood* 88:1098, 1996).

SUMMARY OF THE INVENTION

In one aspect, this invention provides genetically engineered T cells which express and bear on the cell surface membrane a CD20-specific chimeric T cell receptor having an intracellular signaling domain, a transmembrane domain and an extracellular domain. The extracellular domain comprises a CD20-specific receptor. Individual T cells of the invention may be $CD4^+/CD8^-$, $CD4^-/CD8^+$, $CD4^-/CD8^-$ or $CD4^+/CD8^+$. The T cells may be a mixed population of $CD4^+/CD8^-$ and $CD4^-/CD8^+$ cells or a population of a single clone. $CD4^+$ T cells of the invention produce IL-2 when co-cultured in vitro with $CD20^+$ lymphoma cells. $CD8^+$ T cells of the invention lyse $CD20^+$ human lymphoma target cells when co-cultured in vitro with the target cells. The invention includes the CD20-specific chimeric T cell receptors, DNA constructs encoding the receptors, and plasmid expression vectors containing the constructs in proper orientation for expression.

T cells of the invention are referred to in this specification as CD20-specific redirected T cells.

In another aspect, the invention is a method of treating a $CD20^+$ malignancy in a mammal which comprises administering $CD8^+$ CD20-specific redirected T cells to the mammal in a therapeutically effective amount. The $CD8^+$ T cells are preferably administered with $CD4^+$ CD20-specific redirected T cells. In another aspect, the invention is a method of treating a $CD20^+$ malignancy in a mammal which comprises administering $CD4^+$ CD20-specific redirected T cells and $CD8^+$ cytotoxic lymphocytes which do not express the CD20-specific chimeric receptor of the invention, optionally in combination with $CD8^+$ CD20-specific redirected T cells. The invention includes a method of purging $CD20^+$ leukemic stem cells following autologous transplantation for leukemia by administering CD20-specific redirected T cells.

In another aspect, the invention is a method of abrogating any untoward B cell function in a mammal which comprises administering to the mammal CD20-specific redirected T cells in a therapeutically effective amount. These can include antibody mediated autoimmune disease (e.g., lupus or rheumatoid arthritis) as well as any unwanted specific immune response to a given antigen. For example, CD20-specific redirected T cells can be administered in a method of immunosuppression prior to administering a foreign substance such as a monoclonal antibody or DNA or virus or cell in the situation where any immune response would decrease the effectiveness of the foreign substance.

In a preferred embodiment, the CD20-specific redirected T cells express CD20-specific chimeric receptor scFvFc:ζ where scFv designates the $V_H$ and $V_L$ chains of a single chain monoclonal antibody to CD20, Fc represents at least part of a constant region of an $IgG_1$, and ζ represents the intracellular signaling domain of the zeta chain of human CD3. The extracellular domain scFvFc and the intracellular domain ζ are linked by a transmembrane domain such as the transmembrane domain of CD4. In a specific preferred embodiment, the scFvFc:ζ is amino acids 21–633 of Seq. ID No. 2 encoded by DNA construct Seq. ID No. 1.

The invention includes a method of making and expanding the CD20-specific redirected T cells which comprises transfecting T cells with an expression vector containing a DNA construct encoding the CD20-specific chimeric receptor, then stimulating the cells with $CD20^+$ cells, recombinant CD20, or an antibody to the receptor to cause the cells to proliferate.

In another aspect, this invention is a method of stably transfecting and re-directing T cells by electroporation using naked DNA. Most investigators have used viral vectors to carry heterologous genes into T cells. By using naked DNA, we can reduce significantly the time required to produce redirected T cells. "Naked DNA" means DNA encoding a chimeric T cell receptor (TCR) contained in a plasmid expression vector in proper orientation for expression. The electroporation method of this invention produces stable transfectants which express and carry on their surfaces the chimeric TCR (cTCR). "Chimeric TCR" means a receptor which is expressed by T cells and which comprises intracellular signaling, transmembrane and extracellular domains, where the extracellular domain is capable of specifically binding in an MHC unrestricted manner an antigen which is not normally bound by a T cell receptor in that manner. Stimulation of the T cells by the antigen under proper conditions results in proliferation (expansion) of the cells and/or production of IL-2. The CD20-specific chimeric receptor of this invention is an example of a chimeric TCR. However, the method is applicable to transfection with chimeric TCRs which are specific for other target antigens, such as chimeric TCRs that are specific for HER2/Neu (Stancovski et al., supra) ERBB2 (Moritz et al., supra), folate binding protein (Hwu et al., supra), renal cell carcinoma (Weitjens et al., supra), and HIV-1 envelope glycoproteins gp120 and gp41 (Roberts et al., *Blood* 84:2878, 1994).

In a preferred embodiment of transfection method of the invention, the T cells are primary human T cells, such as human peripheral blood mononuclear cells (PBMC), which have previously been considered resistant to stable transfection by electroporation of plasmid vectors. Preferred conditions include the use of DNA depleted of endotoxin and electroporation within about 3 days following mitogenic stimulation of T cells. Following transfection, the transfectants are cloned and a clone demonstrating presence of a single integrated unrearranged plasmid and expression of the chimeric receptor is expanded ex vivo. The clone selected for expansion preferably is $CD8^+$ and demonstrates the capacity to specifically recognize and lyse lymphoma target cells which express the target antigen. The clone is expanded by stimulation with IL-2 and preferably another stimulant which is specific for the cTCR such as, where the receptor includes the zeta chain of CD3, the monoclonal antibody OKT3.

DETAILED DESCRIPTION OF THE INVENTION

EXAMPLE I

Figure 1:
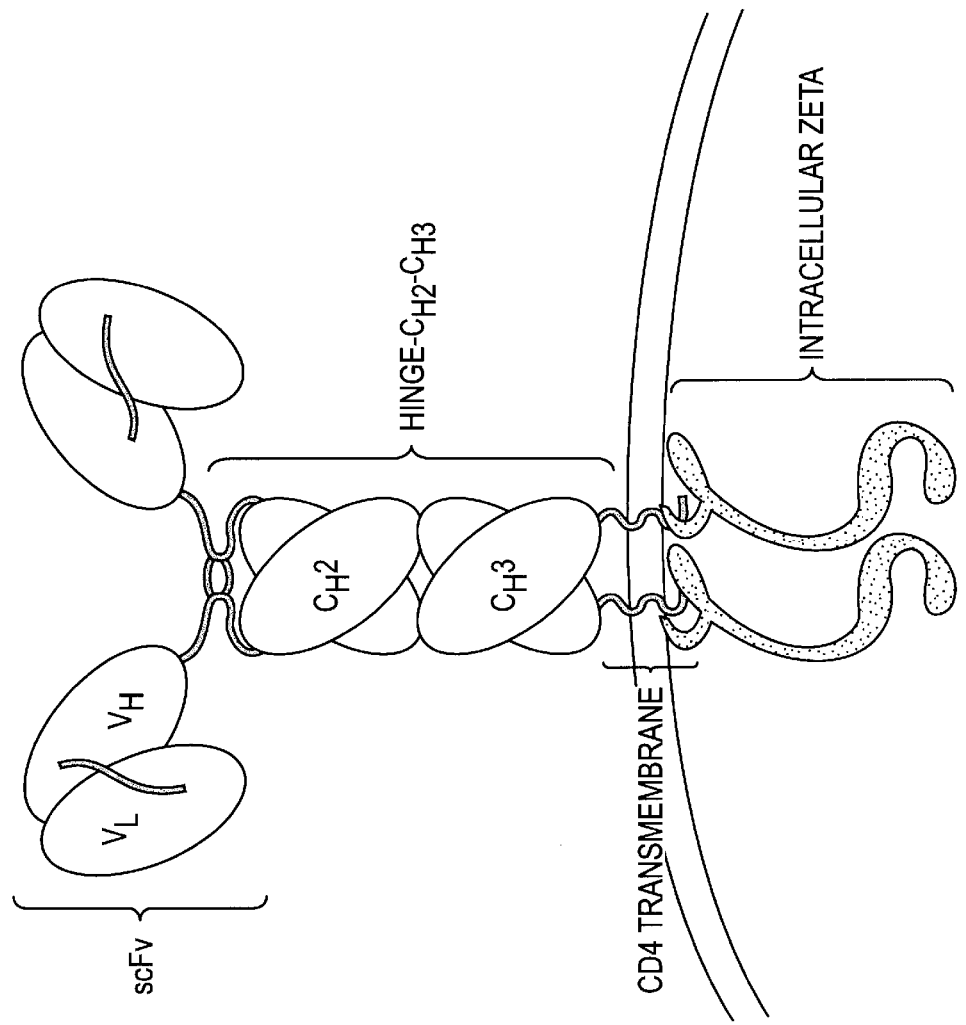
FIG. 1 is a schematic representation of CD20-specific scFvFc:ζ chimeric receptor.
Figure 2A:
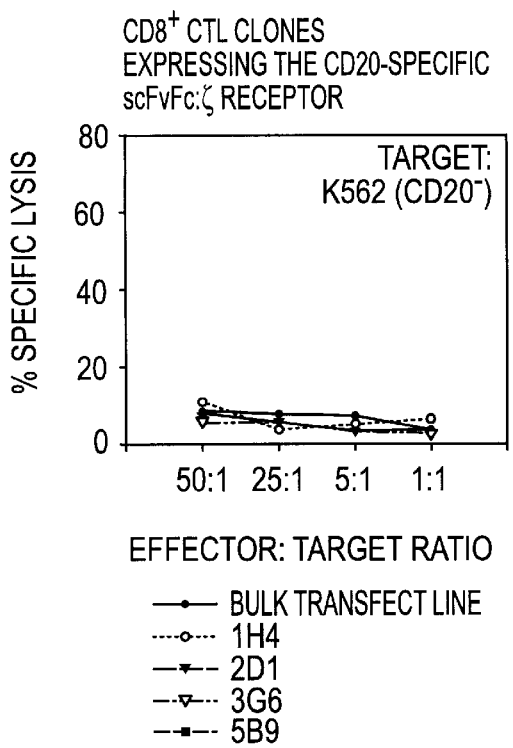
FIG. 2 shows cytolytic activity of $CD8^+$ T cells against a panel of CD 20- and $CD20^+$ human lymphoma targets. The left graphs show activity of $CD8^+$ T cells expressing the CD20-specific scFvFc:ζ chimeric receptor. The right graphs show activity of $CD8^+$ T cells not expressing the CD20-specific scFvFc:ζ chimeric receptor.
Figure 2B:
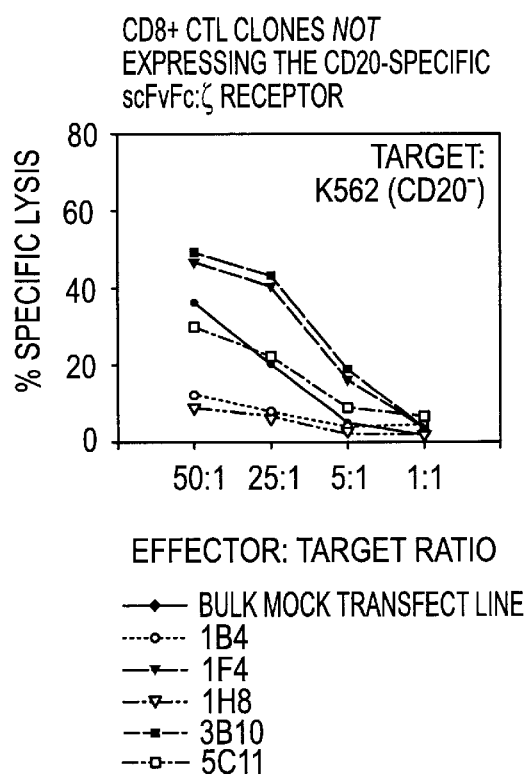
Figure 2C:
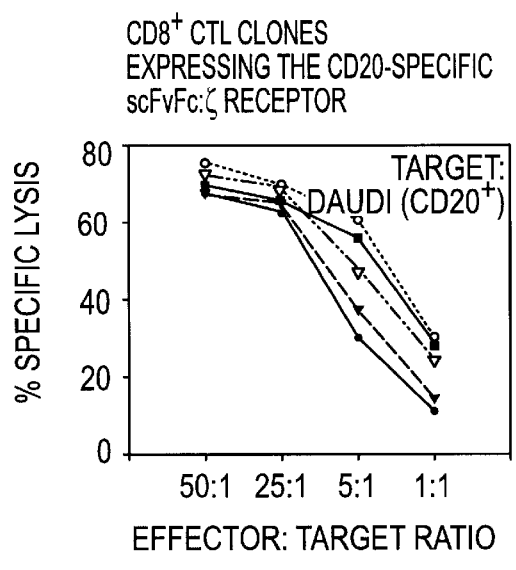
Figure 2D:
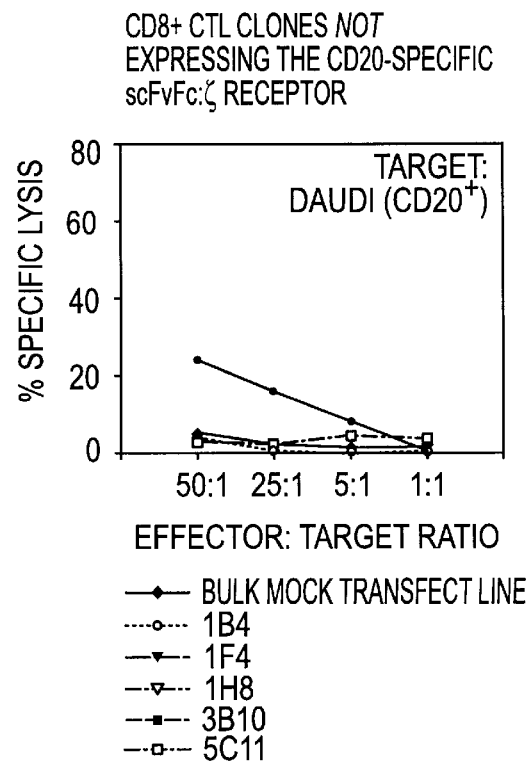
Figure 2E:
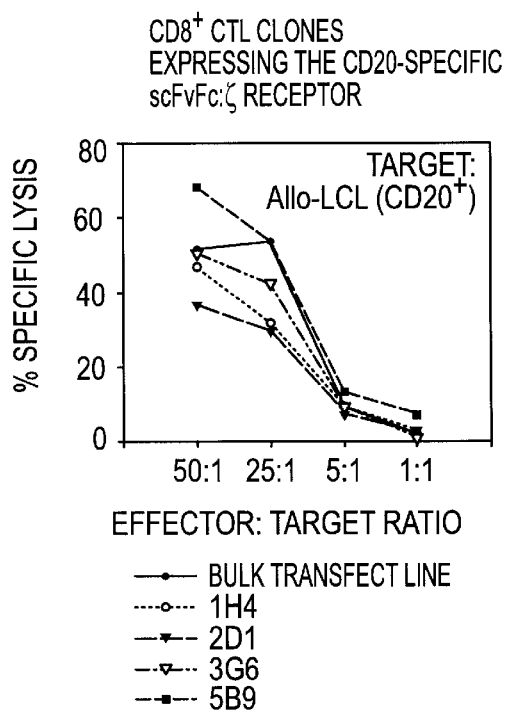
Figure 2F:
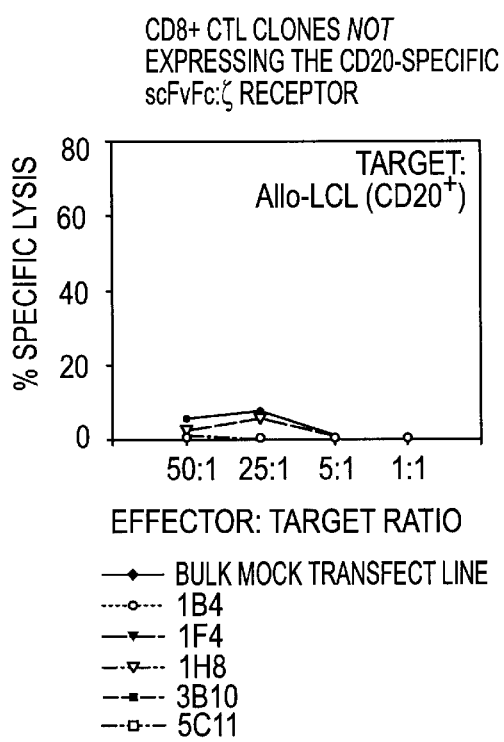
Figure 2G:
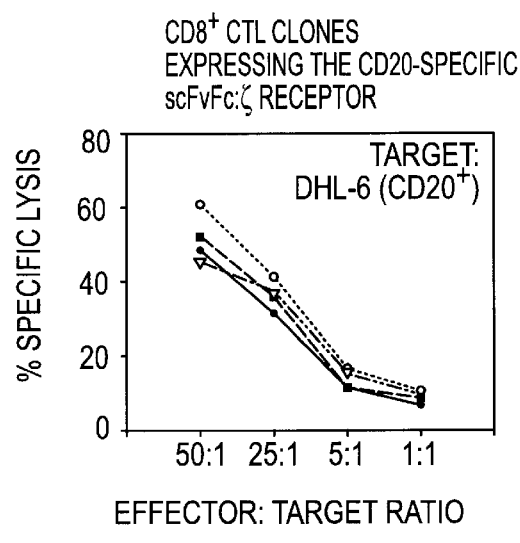
Figure 2H:
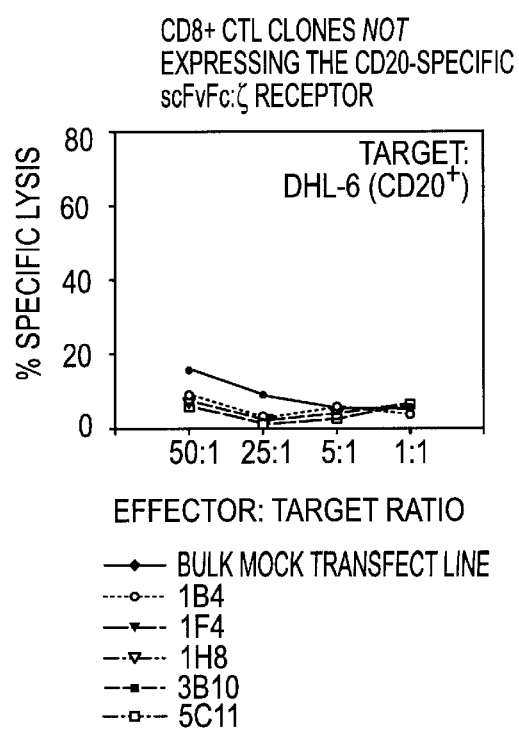

Re-Direction of T-cell Lines Jurkat and 2c

Methods and Materials

Assembly of a CD20-Specific scFvFc:ζ Construct. The nucleotide sequence of the construct and corresponding amino acid sequence of the CD20-Specific scFv:Fc:ζ chimeric receptor are listed in the Sequence Listing as Seq. ID No. 1 and Seq. ID No. 2. The construct was assembled by splice overlap PCR based on the design of Roberts et al., supra. The construct is composed of the following segments, in which the nucleotide and amino acid numbers refer to Seq. ID No. 1 and Seq. ID No. 2.

Ribosome binding sequence, nucleotides 18–26. The consensus ribosome binding sequence, GCCACCACC, was designed in accordance with Kozak, *Nucl. Acids Res.* 15:8125, 1987, and was encoded in a synthetic oligonucleotide.

Signal peptide, nucleotides 27–86, amino acids 1–20. In order to direct the construct to the plasma membrane, the mammalian signal peptide from the murine T84.66 antibody kappa light chain was used (Neumaier, *Cancer Res.* 50:2128, 1990).

Anti-CD20 variable regions: $V_L$—nucleotides 87–404, amino acids 21–126; $V_H$—nucleotides 459–824, amino acids 145–266. Heavy and light chain variable regions were cloned by RT-PCR (reverse transcription-polymerase chain reaction). Total RNA was prepared from $5 \times 10^7$ anti-CD20 Leu-16 hybridoma cells (Becton Dickinson Immunocytometry Systems, Becton Dickinson, San Jose, Calif.) and 5 μg were used in the reaction. Kappa light chain upstream primers VKBi7 (Seq. ID No. 3) and VKBi8 (Seq. ID No. 4) were used. These primers are from Dubel et al., *J. Immunol. Meth.* 175:89, 1994. Heavy chain upstream primers VHBi3 (Seq. ID No. 5), VHBi3c (Seq. ID No. 6) and VHBi3d (Seq. ID No. 7) were used. Downstream primers were: murine heavy chain constant region position 119 to 134 from Honjo, *Cell* 18:559, 1979 (Seq. ID No. 8) and murine kappa constant region position 134–148 from Heiter, *Cell* 22:197, 1980 (Seq. ID No. 9). PCR products were purified, cloned into T-tailed Bluescript (Stratagene) and subjected to DNA sequence analysis. The identity of clones was confirmed by comparison of the predicted amino acid sequences to the sequences of tryptic peptides from the purified CD20 antibody.

GS18 linker, nucleotides 405–458, amino acids 145–266. The heavy and light chain variable regions were fused via an 18 amino acid linker peptide of Seq. ID No. 10. Synthetic oligonucleotide primers encoding this linker sequence were produced and incorporated into the construct by splice overlap PCR.

Hinge—nucleotides 825–872, amino acids 267–282; $CH_2$—nucleotides 873–1202, amino acids 283–392; $CH^3$—nucleotides 1202–1523, amino acids 393–499. The human $IgG_1$ hinge and Fc regions were derived from a cDNA clone encoding a chimeric antibody provided by Dr. Jeffrey Schlom, NCI. The uppermost cys residue in the hinge (normally utilized in the disulfide bridge with the C-terminus of the kappa light chain, and not necessary in this construct) was mutated to ser by PCR mutagenesis.

CD4 Transmembrane region, nucleotides 1524–1590, amino acids 500–521. The transmembrane region was derived from the pT4B plasmid containing human CD4 cDNA, provided by the AIDS Research and Reference Reagent Program (Catalog #157), NIAID.

Zeta chain, nucleotides 1591–1925, amino acids 522–633. The cDNA clone for the human T cell receptor zeta chain was obtained by RT-PCR of total RNA isolated by the guanidinium isothiocyanate method from the Jurkat T-cell line. Primers were designed based on the published nucleotide sequence of the zeta chain (Weissman, *Proc. Nat. Acad. Sci.* 85:9709 (1988) and Moingeon, *Eur. J. Immunol.* 20:1741(1990). The primer sequences were CD3ζFOR (Seq. ID No. 11) (nucleotides 31–52 of CD3 zeta chain) and CD3ζBAC (Seq. ID No. 12) (nucleotides 593–616 of CD3 zeta chain) and included Eco R1 restriction sites for subcloning:

Briefly, 1 μg of total RNA was allowed to react at 37° C. for 15 minutes in a tube containing AMV reverse transcriptase, dNTPs, PCR buffer, forward and backward primers, 3 units of Taq polymerase was then added to the tube and subjected to 30 rounds of PCR amplification, each round consisting of 1 min. at 94° C., 2 min. at 78° C., and 2 min. at 72° C. PCR products were purified and cloned into T-tailed Bluescript and subjected to DNA sequence analysis.

Following confirmation of the correct clone by DNA sequencing, the zeta cytoplasmic domain was incorporated into the final genetic construct by splice overlap PCR. The final construct was flanked by Xba I and Not I restriction sites for directional subcloning into expression vectors. Using these sites the scFvFc:ζ DNA was cloned into the mammalian expression vector pcDNAneo under the control of the CMV immediate-early promoter (Invitrogen, San Diego, Calif.). Correct assembly was confirmed by DNA sequence analysis of the final product. The expressed receptor is schematically represented in FIG. 1. $V_H$ chains 1, $V_L$ chains 2 and linker peptide 3 make up the Fv portion of the receptor. Hinge region 4, $C_H2$ regions 5, and $C_H3$ regions 6 make up the Fc portion of the receptor. Fv and Fc together make up the extracellular domain of the receptor. Numeral 7 denotes the T cell membrane, 8 denotes the CD4 transmembrane domain of the receptor, and 9 denotes the zeta chain intracellular domain of the receptor.

In vitro Propagation of Cell Lines. The Jurkat, Daudi, P815, and K562 cell lines were obtained from ATCC (Rockville, Mo.), the murine allo-specific CTL clone 2c was originated by Dr David Kranz, Univ. of Chicago, and the human lymphoma line DHL-6 was the kind gift of Dr. Michael Cleary, Stanford University. EBV-transformed lymphoblastoid cell lines (LCL) were generated from human EBV infected PBL in the presence of cyclosporin (Pelloquin et al., in vitro Cell Dev. Biol. 22:689, 1986). Cells were grown in RPMI 1640 (GIBCO, Grand Island, N.Y.) supplemented with 2 mmol L-glutamine (Irvine Scientific, Santa Ana, Calif.), 25 mmol HEPES (Irvine Scientific), penicillin 100 U/ml and streptomycin 0.1 mg/ml (Irvine Scientific), and 10% heat inactivated fetal calf serum (Hyclone, Logan, Utah). 2c clones were maintained in culture by restimulating cells every 14 days with irradiated P815 cells. Supplemental human IL-2 (Cetus, Emeryville, Calif.) at 50U/ml was added to 2c cells every 48 hours.

Electroporation and Selection Procedure. pcDNAneo containing the anti-CD20 scFvFc:ζ construct was linearized at a unique PvuII site in the plasmid's ampicillin resistance gene. Linearized plasmid was introduced into Jurkat and 2c clones by electroporation utilizing the BTX Electro Cell Manipulator 600 (Genetronics, San Diego, Calif.) set at 250V, 975 μF, 196 ohms. $2 \times 10^7$ log phase Jurkat or 2c cells used 4 days following antigen stimulation were aliquoted into 0.4 cm electroporation cuvettes in 0.8 ml PBS with 10 mmol $MgCl_2$. 50 μg of plasmid in sterile water was added and incubated for 10 minutes prior to being resuspended in culture media. Forty-eight hours following electroporation, cells were plated in media containing 1 mg/ml active of G418 antibiotic (Mediatech Inc., Herndon, Va.). Drug resistant transfected Jurkat cells were cloned in limiting dilution then expanded for further analysis.

Western Blot Procedure Whole cell lysates of parental Jurkat and 2c cells or their scFvFc:ζ transfectants were generated by lysis of $2 \times 10^7$ washed cells in 1 ml of RIPA buffer (PBS, 1% NP40, 0.5% sodium deoxycholate, 0.1% SDS) containing 1 tablet/10 ml Complete Protease Inhibitor Cocktail (Boehringer Mannheim, Indianapolis, Ind.) and incubated on ice for 80 minutes. Samples of centrifuged lysate supernatant was harvested and boiled in an equal volume of loading buffer under reducing and non-reducing conditions then subjected to SDS-PAGE electrophoresis on a precast 12% acrylamide gel (BioRad, Richmond, Calif.). Following transfer to nitrocellulose, membranes were blocked in blotto solution containing 0.07 gm/ml non-fat dried milk for 2 hours. Membranes were then incubated with primary mouse anti-human CD3ζ monoclonal antibody 8D3 (Pharmingen, San Diego, Calif.) at a concentration of 1 μg/ml for 2 hours, washed then incubated with a 1:500 dilution of goat anti-mouse alkaline phosphatase conjugated secondary antibody for 1 hour. Prior to developing, membranes were washed 4 additional times in T-TBS (0.05% Tween 20 in Tris buffered saline pH 8.0). Membranes were then developed with 30 ml of the manufacturer "AKP" solution (Promega, Madison, Wis.).

FACS Analysis. Jurkat cells and 2c cells were stained with a fluorescein isothiocyanate (FITC)-conjugated goat anti-mouse Fab-specific polyclonal antibody (Sigma, St. Louis, Mo.) and a FITC-conjugated monoclonal mouse anti-human IgG, Fc(gamma) fragment-specific $F(ab')_2$ (Jackson ImmunoResearch, West Grove, Pa.) for analysis of cell surface chimeric receptor expression. $10^6$ cells were washed and resuspended in 100 μl of PBS containing 2% FCS, 0.2 mg/ml $NaN_3$, and 2 μl of antibody. Following a 60 minute incubation on ice cells were washed three times and resuspended in PBS containing 1% paraformaldehyde and analyzed on a MoFlo cytometer (Cytomations, Fort Collins, Colo.).

In vitro Stimulation of Cytokine Production. Jurkat cells expressing the chimeric CD20-specific scFvFc:ζ receptor were evaluated for receptor-mediated triggering of IL-2 production in vitro. $5 \times 10^5$ Jurkat responder cells were co-cultured in 48-well tissue culture plates (Costar, Cambridge, Mass.) with an equal number of irradiated stimulator cells in a 1 ml volume. Blocking anti-CD20 Leu-16 monoclonal antibody was added to indicated wells containing stimulator cells at a concentration of 20 μg/ml 30 min prior to the addition of responder cells. Plates were incubated for 48 hours at which time culture supernatants were harvested and evaluated for IL-2 protein concentration. An ELISA assay for IL-2 was carried out using the R&D Systems (Minneapolis, Minn.) kit per manufacturer instructions. Each sample was tested in duplicate wells undiluted and diluted 1:5. The developed ELISA plate was evaluated on a microplate reader and IL-2 concentrations determined by extrapolation from a standard curve. Results are reported as picograms/ml.

Chromium Release Assay. The cytolytic activity of 2c and 2c transfectants was assayed by employing $^{51}$Cr-labeled P815, K562, Daudi, DHL-6, and LCL cell lines. Briefly, 2c effectors were assayed 8–12 days following stimulation with irradiated P815 cells. Effectors were harvested, washed, and resuspended in assay media; $2.5 \times 10^5, 1 \times 10^5, 0.5 \times 10^5$, and $0.1 \times 10^5$ effectors were cultured in triplicate at 37° C. for 4 hours with $10^4$ target cells in V-bottom microtiter plates (Costar, Cambridge, Mass.). After centrifugation and incubation, 100λ aliquots of cell-free supernatant were harvested and counted. Per cent specific cytolysis was calculated as follows:

$$\frac{(\text{Experimental } ^{51}\text{release}) - (\text{control } ^{51}Cr \text{ release}) \times 100}{(\text{Maximum } ^{51}Cr \text{ release}) - (\text{control } ^{51}Cr \text{ release})}$$

Control wells contained target cells incubated in the presence of target cells alone. Maximum $^{51}$Cr released was determined by measuring the $^{51}$Cr content of labeled cells in the presence of 2% SDS.

Results

The CD20-specific scFvFc:ζ receptor protein is expressed in Jurkat and 2c cells. To determine whether the CD20-specific scFvFc:ζ construct could be expressed as an intact chimeric protein, Jurkat and 2c cells were transfected with the receptor cDNA cloned into pcDNAneo under the transcriptional control of the CMV immediate-early promoter. Linearized plasmid was electroporated under optimized conditions and stable transfectants selected by addition of G418 to cultures. Jurkat clones were isolated by limiting dilution while 2c transfectants were maintained as a bulk line. A Western blot of reduced and non-reduced transfectant whole cell lysates separated on a 12% SDS-PAGE gel demonstrated the presence of endogenous zeta having a molecular weight of approximately 16kD as well as a band corresponding to the expected molecular weight (66 kDa) of the CD20-specific scFvFc:ζ receptor. When lysates were generated under non-reducing conditions, the endogenous zeta band migrated at approximately 32 kD as expected for a homodimer while the chimeric receptor band migrated at a molecular weight of approximately 132 kD.

The CD20-specific scFvFc: receptor protein is present on the cell surface of Jurkat and 2c cells. Export of the CD20-specific receptor to the plasma membrane of Jurkat and 2c cells was assessed by flow cytometric analysis of transfectants with a FITC-conjugated goat anti-mouse Fab-specific antibody and a goat anti-human Fc (gamma) antibody. The murine Fab epitope is expected to be reconstituted in the scFv portion of the chimeric receptor while the human Fcγ epitope is the membrane proximal portion of the receptor's extracellular domain. Analysis of surface expression, as detected with FITC-conjugated anti-Fab antibody, of chimeric receptor expression on a representative Jurkat clone transfectant three weeks following electroporation showed a log shift in fluorescence compared to parental Jurkat. Similar analysis of a bulk population of 2c transfectants stained with anti-human Fc (gamma) revealed a similar pattern of binding of FITC-conjugated antibody. Receptor expression remained stable over a three month period of continuous culture of cells in G418.

CD20 expressed on lymphoma cells triggers IL-2 production by Jurkat cells expressing the CD20-specific scFvFc:ζ receptor. The capacity of the CD20-specific scFvFc:ζ receptor to transduce an activation signal in Jurkat cells sufficient for triggering IL-2 production was determined by culturing Jurkat transfectant clones with CD20-expressing lymphoma cells in vitro and quantitating IL-2 concentrations in supernatants by ELISA. In a representative experiment, parental Jurkat cells produced IL-2 in response to mitogenic doses of OKT3 (anti-CD3 monoclonal antibody, Ortho) in combination with PMA, but did not produce IL-2 when co-cultured with $CD20^-$ K562 cells, or $CD20^+$ DHL-6 or LCL. In contrast, Jurkat transfectants expressing the CD20-specific scFvFc:ζ receptor produced IL-2 when co-cultured with a panel of $CD20^+$ lymphoma cells. Addition of CD20-specific monoclonal antibody to co-cultured Jurkat transfectants and LCL decreased IL-2 concentrations measured in supernatants by 60%.

CD20 expressed on lymphoma cells triggers cytolytic activity of 2c cells expressing the CD20-specific scFvFc:ζ receptor. 2c is an extensively characterized murine cytolytic T cell clone specific for $H-2^{d39}$. This clone requires both antigen stimulation and IL-2 for in vitro propagation. Electroporated 2c cells were selected in bulk with G418. Following confirmation of scFvFc:ζ expression by Western blot and FACS, this line was evaluated for redirected CD20-specific cytolytic activity in a 4-hour chromium release assay. Lysis of $CD20^+$ human lymphoma targets Daudi, DHL-6, and LCL was observed by 2c transfectants while the parental and transfected lines displayed equivalent lysis of P815, a murine $H-2^d$ mastocytoma line recognized by 2c via its endogenous TCR. Neither parental 2c nor scFvFc:ζ 2c transfectants lysed the $CD20^-$ target K562. The transfected cell line was retested for CD20-specific cytolytic activity over a three month period and was found to have stable lytic activity.

EXAMPLE II

Redirection of Normal, Non-malignant Human T Cells

Methods and Materials

Plasmid DNA. The CD20-specific scFvFc:ζ construct was prepared as described in Example I. This cDNA was ligated into the multiple cloning site of the mammalian expression vector pcDNAneo (Invitrogen, San Diego, Calif.). The plasmid was propagated in E. coli and purified with Qiagen's Endo-Free Maxi prep kit per the manufacturer's instructions (Qiagen Inc., Valencia, Calif.). The plasmid was linearized at a unique PvuI site in the ampicillin resistance gene. Following digestion, plasmid DNA was precipitated with a 1:10 volume of 3M sodium acetate and two volumes of EtOH, washed in 70% EtOH, and resuspended in sterile pyrogen-free distilled water. Vector DNA was stored in aliquots at −20° C. until used for electroporation.

Cell Lines. Daudi, K562, DHL-6 and LCL lines were obtained and grown as described in Example I.

Human PBMC Isolation and Activation. Heparinized peripheral blood from normal donors was diluted 1:1 with PBS containing 0.526 mmol EDTA. PBMC were isolated by density gradient centrifugation over Ficoll-Paque (Pharmacia Biotech Inc., Piscataway, N.J.), washed twice in PBS-EDTA, once in PBS then resuspended in culture media at $10^6$ cells per ml. PBMC were cultured in 6-well tissue culture plates containing 10 ml/well of PBMC cell suspension and PHA-P 0.5 μg/ml. (Murex, UK). Twenty-four hours after initiation of culture recombinant IL-2 was added at 25 U/ml. Approximately 72 hours after the initiation of culture activated PBMC were subjected to electroporation.

PBMC Electroporation. PvuII linearized plasmid pcDNAneo containing the CD20-Specific scFcFv:ζ, described above, was introduced into PHA-activated human PBMC by electroporation utilizing the BTX Electro Cell Manipulator 600 (Genetronics, San Diego, Calif.) set at 250V, 950 μF, 129Ω. $5×10^6$ PBMC were aliquoted into 0.4 cm electroporation cuvettes (Biorad, Richmond, Calif.) in 0.25 ml of culture media containing 25 U/ml recombinant human IL-2 (rhIL-2). 25 μg of linear plasmid in 12.5 μL sterile water was added to the cells and incubated for 10 minutes on ice. Following a single electrical pulse, cells were again incubated on ice for 10 minutes prior to being resuspended in culture media. Typically, the contents of four cuvettes were pooled and resuspended in 10 ml of culture media containing 25 U/ml rhIL-2, then placed in a single well of a 6-well tissue culture plate.

Selection of T Cell Transfectants. Forty-eight hours following electroporation, G418 antibiotic (Calbiochem, La Jolla, Calif.) was added to wells containing electroporated PBMC at an active drug concentration of 0.9 mg/ml. Cells were periodically split to maintain their concentration at approximately $10^6$ viable cells/ml. IL-2 at a concentration of 25 U/ml was added every other day to culture. Twelve days following the initiation of culture, viable cells were harvested by density gradient centrifugation on Ficoll-Paque. Washed viable cells were subjected to rapid expansion by co-culture in T25 flasks containing $25×10^5$ allogeneic irradiated PBMC, $5×10^6$ allogeneic irradiated LCL, and 30 ng/ml OKT3. Beginning 24 hours following seeding, flasks received 25 U/ml rhIL-2 on alternate days. On day five of culture, 0.9 mg/ml G418 was added to flasks. Fourteen days after seeding flasks, no viable mock transfected PBMC were detected by trypan exclusion, while plasmid transfected PBMC demonstrate outgrowth of T cells. This procedure has yielded neo-resistant T cell lines in each of over fifteen separate electroporations.

T cell cloning and expansion. G418-resistant PBMC were cloned at 0.3 cells/well in 96-well U-bottom plates containing $5×10^6$ allogeneic irradiated PBMC feeder cells and $1×10^3$ irradiated allogeneic LCL per well in 200λ of culture media containing 30 ng/ml OKT3 and 50 U/ml rhIL-2. Five days after cloning, G 418 at a final concentration of 0.9 mg/ml was added to wells. Cloning plates were screened visually for wells with cellular outgrowth between 12–16 days after plating. Positive wells were harvested and restimulated every 14 days with OKT3 and IL-2 on a double feeder layer of irradiated PBMC and LCL, as described above. G418 was added to culture 5 days after each restimulation at 0.9 mg/ml.

FACS Analysis. Cloned human T cell transfectants were stained with a panel of monoclonal antibodies to establish their cell-surface phenotype. This panel included fluorescein isothiocyanate (FITC)-conjugated anti-TCR α/β, anti-CD4, and anti-CD8, as well as a FITC-conjugated murine isotype control (Becton Dickinson, San Jose, Calif.). $10^6$ cells were washed and resuspended in 100 μL PBS containing 2% FCS, 0.2 mg/ml NaN$_3$ and 2 μL of the manufacture's stock antibody preparation. Following a 60-minute incubation on ice, cells were washed three times and resuspended in PBS containing 1% paraformaldehyde and analyzed on a MoFlo cytometer (Cytomations, Fort Collins, Colo.).

Detection of Plasmid Integration by Fluorescence in Situ Hybridization (FISH). The plasmid pcDNAneo was labeled with digoxigenin-dUTP using a nick translation kit (Vysis, Inc., Downers Grove, Ill.). Briefly, 100 ng of labeled DNA was precipitated and dissolved in 10 μL of Hybrisol VII (Oncor, Gaithersburg, Md.). The probe was denatured at 72° C. for 5 min before use. Cells were harvested per standard cytogenetic technique by treatment with 0.05 μg/ml colcemid (Irvine Scientific, Irvine, Calif.) for 40 min, and subsequently exposed to a hyptonic solution of 0.4% KCl at 37° C. for 20 min. The cells were then fixed with Carnoy's fixative (1 acetic acid: 3 methanol). For sequential FISH analysis, slides were G-banded using trypsin-Giemsa, photographed, and destained; otherwise, slides were digested with 12 μg/ml pepsin (Sigma) in 0.01 N HCL at 37° C. for 3 min. Chromosomal DNA was denatured by submerging slides in 70% formamide/2×SSC, pH 7.0 at 72° C. for 2 min. Denatured probe (10 μL) was applied to each slide and incubated at 37° C. overnight. Nonspecific probe binding was purged by sequential washes of 50% formamide/2×SSC, pH 7.0 at 39° C. for 10 min, and 2×SSC at 37° C. for 8 min. Signals were detected using a rhodamine detection kit for digoxigenin (Oncor). Chromosomes were counter stained with DAPI (Oncor). Signals were observed and captured with a NIKON Labophot-2 fluorescence microscope equipped with a PSI Imaging System (Perceptive Scientific Instruments Inc., League City, Tex.).

Southern Blot Analysis for Vector Copy Number and Rearrangement. Southern blot analysis was carried out using zeta- and neomycin DNA probes. The DNA fragment used as a zeta-specific probe was generated by PCR using the CD20-specific scFvFc:ζ-pcDNAneo plasmid as template. The forward primer zetaforward (5'-TTCAGCAGGAGCGCAGCAGC-3')(Seq. ID No. 13) and the reverse primer zeta$_{reverse}$ (5'-TAGCGAGGGGGCAGGGCCTG-3') (Seq. ID No. 14) were used at a concentration of 50 picomolar. PCR conditions were as follows; 94° C., 1 min; 60° C., 1 min; 72° C., 2 min; 24 cycles. This PCR reaction generated a 329 basepair fragment comprising the zeta gene's exons III through VIII that encode the intracellular portion of this molecule. The Neo-specific DNA probe was the 420 basepair MscI/NaeI restriction fragment isolated from pcDNAneo. Probe DNA was $^{32}$p labeled using a random primer labeling kit (Boehringer Mannheim, Indianapolis, Ind.).

Genomic DNA was isolated per standard technique (Sambrook et al., *Molecular Cloning: A Laboratory Manual*, 2d Edition, Cold Spring Harbor Laboratory, Cold Spring Harbor, N.Y., 1989, p9.16). Ten micrograms of genomic DNA from T cell lines and clones were digested overnight at 37° C. with 40 units of XbaI and HindIII and then electrophoretically separated on a 0.85% agarose gel. DNA was then transferred to nylon filters (BioRad, Hercules, Calif.) using an alkaline capillary transfer method. Filters were hybridized overnight with either zeta- or neomycin-specific $^{32}$P-labeled probes in 0.5 M Na$_2$PO$_4$, PH 7.2, 7% SDS, containing 10 μg/ml salmon sperm DNA (Sigma) at 65° C. Filters were then washed four times in 40 mM Na$_2$PO4, pH 7.2, 1% SDA at 65° C. and then visualized using a phosphoimager (Molecular Dynamics, Sunnyvale, Calif.).

Western Blot Procedure. Whole cell lysates of bulk untransfected and transfected T cell lines and each of nine cloned transfectants were generated by lysis of 2×10$^7$ washed cells in 1 ml of RIPA buffer (PBS, 1% NP40, 0.5% sodium deoxycholate, 0.1% SDS) containing 1 tablet/10 ml Complete Protease Inhibitor Cocktail (Boehringer Mannheim). After an eighty minute incubation on ice, aliquots of centrifuged whole cell lysate supernatant were harvested and boiled in an equal volume of loading buffer under reducing conditions then subjected to SDS-PAGE electrophoresis on a precast 12% acrylamide gel (BioRad). Following transfer to nitrocellulose, membranes were blocked in blotto solution containing 0.07 gm/ml non-fat dried milk for 2 hours. Membranes were washed in T-TBS (0.05% Tween 20 in Tris buffered saline pH 8.0) then incubated with primary mouse anti-human CD3ζ monoclonal antibody 8D3 (PharMingen, San Diego, Calif.) at a concentration of 1 μg/ml for 2 hours. Following an additional four washes in T-TBS, membranes were incubated with a 1:500 dilution of goat anti-mouse IgG alkaline phosphatase-conjugated secondary antibody for 1 hour. Prior to developing, membranes were rinsed in T-TBS then developed with 30 ml of "AKP" solution (Promega, Madison, Wis.) per the manufacturer's instructions.

Chromium Release Assay. The cytolytic activity of bulk CD20-specific scFvFc:ζ PBMC transfectants and cloned CD8$^+$ CTL transfectants was quantitated in standard 4-hr. chromium release assays by employing $^{51}$CR-labeled K562, Daudi, DHL-6, and LCL cell lines. Briefly, T cell effectors were assayed 12–14 days following stimulation with OKT3. Effectors were harvested, washed, and resuspended in assay media; 2.5×10$^5$, 1×10$^5$, and 0.1×10$^5$ effectors were plated in triplicate at 37° C. for 4 hours with 10$^4$ target cells in V-bottom microtiter plates (Costar, Cambridge, Mass.). After centrifugation and incubation, 100 μL aliquots of cell-free supernatant were harvested and counted. Percent specific cytolysis was calculated by the formula given in Example I.

Control wells contained target cells incubated in assay media. Maximum $^{51}$Cr release was determined by measuring the $^{51}$Cr content of target cells lysed with 2% SDS.

Results

Electroporated linear plasmid DNA is chromosomally integrated into primary human T cells present in PHA-activated PBMC. PBMC activated with the T cell mitogen PHA were evaluated for their capacity to chromosomally integrate naked linear plasmid DNA following electroporation. After optimizing electroporation parameters for transient plasmid transfection by expression of green fluorescent protein (data not shown), culture systems were developed to retrieve stable T cell transfectants, as illustrated in Table. 1:

TABLE 1

| Day 0 | Isolate PBMC/PHA-P Activate |
|---|---|
| Day 3 | Electroporate |
| Day 5 | Add G418 |
| Day 12 | Ficoll and Restimulate OKT3/IL-2 |

TABLE 1-continued

| | |
|---|---|
| Day 26 | Clone with OKT3 |
| Day 38 | Restimulate Clones with OKT3/IL-2 |
| Day 50 | Expand Clones which Express Chimeric Receptor |

Typically, two weeks following electroporation with linear plasmid DNA, the outgrowth of cells in the presence of G418 was observed. This procedure has yielded G418-resistant T cell lines in each of over fifteen separate electroporations.

Cloned G418-resistant PBMC transfectants were evaluated for their cell surface phenotype by FACS: each clone was TCR α/β$^+$, CD4$^-$ and CD3$^+$. Nine clones were expanded for further analysis. The integration status of the scFvFc:ζ-pcDNAneo vector was first assessed by FISH using a digoxigenin-labeled probe synthesized from the 5.4 kb pcDNAneo plasmid without the scFvFc:ζ insert. In a representative FISH result, an untransfected CD8$^+$ T cell clone demonstrated lack of chromosomal signal while G418 resistant CD8$^+$ T cell clone transfectants demonstrated a chromosomal signal doublet on metaphase spreads consistent with plasmid integration. A single clone had a uniform FISH signal chromosomal location amongst individual cells while different clones demonstrated distinct sites of integration on different chromosomes. Detailed evaluation of G-banded chromosomes containing FISH signals revealed the following locations of plasmid DNA integration: clone 3B10 at 2q33, clone 1B4 at 3p25.1, and clone 3G6 at 13q22. All of the nine clones evaluated demonstrated a single FISH signal consistent with one site of chromosomal integration.

Human CD8$^+$ T cell clones can be isolated from electroporated PBMC that have a single copy of unrearranged plasmid vector integrated at a single chromosomal site. Southern blot analysis was performed on bulk transfected lines and the panel of nine CD8$^+$ T cell clones in order to validate and extend the results obtained by FISH. The copy number of integrated plasmid and frequency of plasmid rearrangement was also assessed. Genomic T cell DNA from stably transfected bulk PBMC and the panel of CD8$^+$ CTL clones was isolated, digested with the restriction endonucleases XbaI and HindIII that flank the scFvFc:ζ construct, separated by electrophoresis, and blotted onto nylon filters. Probing the Southern blot with a $^{32}$P-labeled cDNA fragment of the neomycin resistance gene revealed a single band in each of the nine clones while the bulk T cell line had multiple bands. Untransfected T cells fail to hybridize this probe. These results are consistent with the FISH data with respect to a single plasmid integration event per T cell clone. The heterogeneity of Neo probe band size observed among different cloned T cell transfectants is indicative of multiple integration events occurring within the population of T cells being electroporated rather than the isolation of multiple daughter cells arising from an exceedingly rare stable integration event. After stripping the nylon filter of the Neo probe, a second probe consisting of the cDNA sequence of the intracellular portion of the TCR zeta chain was annealed. XbaI/HindIII digested genomic DNA from untransfected T cells revealed two bands consistent with the genomic zeta gene having one of these restriction sites within one of its seven introns (Jensen et al., *J. Immunol.* 148:2563, 1992). Seven of nine clones demonstrated the expected 1.9-kb band liberated by endonuclease digestion of the XbaI and HindIII sites present in the integrated plasmid sequence in addition to the two genomic zeta bands. Two clones (1B4 and 1H8) had a 7.2-kb band suggestive of rearrangement of the plasmid or loss of one or both restriction sites around the scFvFc:ζ insert in pcDNAneo. Utilizing a phosphoimager the band intensities were quantitated to determine the copy number of plasmid DNA. A single plasmid copy number would be expected to have half the arbitrary intensity of the summed genomic zeta bands intensities. This analysis revealed normalized values of plasmid copy number between 1.0 and 1.3 consistent with a single plasmid copy number in each of the seven clones with unrearranged 1.9-kb zeta signals. Values slightly larger than 1.0 are expected since DNA transfer onto nitrocellulose is more efficient for smaller sized DNA fragments (Sambrook et al., supra).

A subset of transfected CD8$^+$ CTL clones expanded to large numbers in vitro express the CD20-specific scFvFc:ζ immunoreceptor. Neo-resistant CD8$^+$ T cell clones transfected with the CD20-specific scFvFc:ζ-pcDNAneo plasmid vector were expanded over six weeks to cell numbers in excess of 10$^9$. This was accomplished utilizing a T cell rapid expansion protocol developed by Riddell et al. (Riddell et al., *Science* 257:238, 1992). Briefly, flasks containing soluble OKT3 and a double feeder cell layer of irradiated PBMC and LCL were seeded with 10$^5$ T cells harvested from cloning wells and expanded over two weeks with alternate day addition to culture of rhIL-2 at 50 U/ml. Clones were recursively expanded every two weeks in this format resulting in the generation of over 10$^9$ cells after three re-stimulation cycles. Following expansion, bulk T cell transfectants, CTL clones, and control non-transfected T cells, were harvested and evaluated by Western blot for expression of the chimeric scFvFc:ζ protein. In a representative Western blot result from reduced whole cell lysates probed with an anti-zeta monoclonal antibody, each T cell line and clone displayed a 21-kDa band consistent with wild-type zeta chain. Four of the nine clones demonstrated a second band of approximately 66-kDa consistent with the chimeric zeta chain. Of note, neither clone with disrupted plasmid vector sequence as detected by Southern blot expressed chimeric receptor.

Ex vivo expanded CD20-specific scFvFc:ζ-expressing primary human CD8$^+$ CTL clones lyse human CD20$^+$ lymphoblastoid cells and the human lymphoma cell lines Daudi and DHL-6. The CD20-specific cytolytic activity of scFvFc:ζ-transfected CD8$^+$ CTL clones was determined following ex vivo expansion of cells. 4-hr chromium release assays were performed on bulk transfected T cell lines and clones 12-14 following their last stimulation with OKT3. Distinct patterns of cytolytic activity by clones were observed which correlated precisely with expression of the CD20-specific scFvFc:ζ receptor as determined by Western blot. Each of the four clones with chimeric receptor expression lysed HLA-mismatched CD20$^+$ LCL and the human CD20$^+$ lymphoma cell lines Daudi and DHL-6. These clones did not lyse the CD20$^-$ human K562 cell line. Clones which failed to demonstrate chimeric receptor expression by Western also failed to lyse each of the CD20$^+$ target cell lines. Three of these clones demonstrated NK-like reactivity in that they lysed K562 targets. Clones expanded for over three months in culture retained their CD20-specific cytolytic activity.

Other CD20-specific Chimeric T Cell Receptors

The invention has been described primarily with reference to the specific scFcFv:ζ construct and receptor of Seq. ID No. 1 and 2, but the invention is not limited to that specific construct and receptor. The scFv portion can be replaced by any number of different CD20 binding domains, ranging from a minimal peptide binding domain, to a structured CD20 binding domain from a phage library, to antibody like domains using different methods to hold the heavy and light chain together. The arrangement could be multimeric such as a diabody. The secreted form of the antibody forms multimers. It is possible that the T cell receptor variant is also a multimer. The multimers are most likely caused by cross pairing of the variable portion of the light and heavy chains into what has been referred to by Winters as a diabody.

The hinge portion of the construct can have multiple alternatives from being totally deleted, to having the first cysteine maintained, to a proline rather than a serine substitution, to being truncated up to the first cysteine. The Fc portion can be deleted, although there is data to suggest that the receptor preferably extends from the membrane. Any protein which is stable and dimerizes can serve this purpose. One could use just one of the Fc domains, e.g, either the $C_H2$ or $C_H3$ domain.

Alternatives to the CD4 transmembrane domain include the transmembrane CD3 zeta domain, or a cysteine mutated CD 3 zeta domain, or other transmembrane domains from other transmembrane signaling proteins such as CD16 and CD8. The CD3 zeta intracellular domain was taken for activation. Intracellular signaling portions of other members of the families of activating proteins can be used, such as FcyyIII and FceRI See Gross et al., Stancovski et al., Moritz et al., Hwu et al., Weijtens et al., and Hekele et al., supra, for disclosures of cTCR's using these alternative transmembrane and intracellular domains.

Cellular Immunotherapy Using Redirected T Cells

BACKGROUND

The strategy of isolating and expanding antigen-specific T cells as a therapeutic intervention for human disease has been validated in clinical trials. Riddell et al., *Science* 257:238, 1992; Walter et al., *N. Engl. J. Med.* 333:1038, 1995; Heslop et al., Nat. Med. 2:551, 1996. Initial studies have evaluated the utility of adoptive T cell therapy with CD8$^+$ cytolytic T cell (CTL) clones specific for cytomegalovirus-encoded antigens as a means of reconstituting deficient viral immunity in the setting of allogeneic bone marrow transplantation and have defined the principles and methodologies for T cell isolation, cloning, expansion and re-infusion (Riddell et al., supra). A similar approach has been taken for controlling post-transplant EBV-associated lymphoproliferative disease. EBV-specific donor-derived T cells have the capacity to protect patients at high risk for this complication as well as eradicate clinically evident disease which mimics immunoblastic B cell lymphoma (Heslop et al., supra). These studies clearly demonstrate that adoptively transferred ex vivo expanded T cells can mediate antigen-specific effector functions with minimal toxicities and have been facilitated by targeting defined virally-encoded antigens to which T cell donors have established immunity.

The application of adoptive T cell therapy as a treatment modality for human malignancy has been limited by the paucity of molecularly-defined tumor antigens capable of eliciting a T cell response and the difficulty of isolating these T cells from the tumor-bearing host. Consequently, initial cellular immunotherapy trials utilizing autologous antitumor effector cells relied on antigen nonspecific effector cells such as lymphokine activated killer (LAK) cells which had limited efficacy and pronounced toxicities (Rosenberg et al., *J. Natl. Cancer Inst* 85:622 and 1091, 1993). In an attempt to enhance the tumor-specificity of infused effector cells, IL-2 expanded tumor-infiltrating lymphocytes (TIL) were evaluated (Rosenberg et. al., *N. Engl. J. Med.* 319:1676, 1988). Responses to TIL infusions were sporadic due in part to the heterogeneous population of cells expanded with unpredictable antitumor specificities. Patients with melanoma and renal cell carcinoma however occasionally manifested striking tumor regressions following TIL infusions and tumor-specific MHC-restricted T cell clones have been isolated from these patients. Recently, expression cloning technologies have been developed to identify the genes encoding tumor antigens thereby facilitating the development of recombinant DNA-based vaccine strategies to initiate or augment host antitumor immunity, as well as in vitro culture systems for generating tumor-specific T cells from cancer patients (Van Pel et al., *Immunol. Rev.* 145:229, 1995). Clinical trials utilizing autologous tyrosinase-specific CTL for the treatment of melanoma are currently underway and will likely provide major insights into the efficacy of targeting tumors with antigen-specific MHC-restricted T cell clones [S. Riddell, personal communication].

The inclusion of hematogenous malignancies as targets for T cell therapy is warranted based on the observed graft versus leukemia (GVL) effect observed in the setting of allogeneic BMT and the capacity of donor buffy coat infusions to have anti-leukemic activity (Porter et al., *Cancer Treat Res.* 77:57, 1997). At present, it is clear that T cells present in the marrow graft mount a response to host minor histocompatibility antigens (mHA's) contributing to graft versus host disease and there is increasing evidence that there may be T cell specificities for GVL that are distinct from those of GVHD on the basis of restricted tissue expression of a subset of mHA's (van Lochem et al., *Bone Marrow Transplant.* 10:181, 1992). Nevertheless, the susceptibility of malignant B cells to CTL recognition and lysis is well documented (Cardoso et al., *Blood* 90:549, 1997; Dolstra et al., *J. Immunol.* 158:560, 1997). Efforts to target B cell lymphoma with MHC-restricted CTL have focused on the lymphoma clone's idiotype as a tumor-specific antigen. Murine models have demonstrated that CTL responses can be generated to immunoglobulin variable regions and that lymphoma cells process and present these determinants for T cell recognition (Dohi et al., *J. Immunol.* 135:47, 1985; Chakrabarti et al., *Cell Immunol.* 144:455, 1992). Although these strategies are potentially tumor-specific, they are also patient specific thus making large scale application difficult.

Endowing T cells with a desired antigen specificity based on genetic modification with engineered receptor constructs is an attractive strategy since it bypasses the requirement for retrieving antigen-specific T cells from cancer patients and, depending on the type of antigen recognition moiety, allows for targeting tumor cell-surface epitopes not available to endogenous T cell receptors. Studies to define the signaling function of individual components of the TCR-CD3 complex revealed that chimeric molecules with intracellular domains of the CD3 complex's zeta chain coupled to extracellular domains which could be crosslinked by antibodies were capable of triggering biochemical as well as functional activation events in T cell hybridomas (Irving et al., *Cell* 64:891, 1991). Recent advances in protein engineering have provided methodologies to assemble single chain molecules consisting of antibody variable regions connected by a flexible peptide linker which recapitulate the specificity of the parental antibody (Bird et al., *Science* 242:423, 1988 and 244(4903):409, 19989. Several groups have now reported on the capacity of chimeric single chain receptors consisting of an extracellular scFv and intracellular zeta domain to re-direct T cell specificity to tumor cells expressing the antibody's target epitope; receptor specificities have included HER2/Neu, and less well characterized epitopes on renal cell and ovarian carcinoma (Gross et al., Eshhar et al., Stancovski et al., Moritz et al., Huw et al., Weitjens et al, supra). An idiotype-specific scFv chimeric TCR has been described which recognizes the idiotype-expressing lymphoma cell's surface immunoglobulin as its ligand (Gross et al., *Biochem. Soc. Trans.* 23:1079, 1995). Although this approach swaps a low affinity MHC-restricted TRC complex for a high affinity MHC-unrestricted molecular linked to an isolated member of the CD3 complex, these receptors do activate T cell effector functions in primary human T cells without apparent induction of subsequent anergy or apoptosis (Weitjens et al., supra). Murine model systems utilizing scFv:ζ transfected CTL demonstrate that tumor elimination only occurs in vivo if both cells and IL-2 are administered, suggesting that in addition to activation of effector function, signaling through the chimeric receptor is sufficient for T cell recycling (Hekele et al., supra).

Although chimeric receptor re-directed T cell effector function has been documented in the literature for over a decade, the clinical application of this technology for cancer therapy is only now beginning to be applied. ex vivo expansion of genetically modified T cells to numbers sufficient for re-infusion represents a major impediment for conducting clinical trials. Not only have sufficient cell numbers been difficult to achieve, the retention of effector function following ex vivo expansion has not been routinely documented in the literature.

Treatment of CD20+Malignancies with CD20-specific Redirected T Cells

This invention represents the first attempt to target a universal B cell lymphoma cell-surface epitope with CD20-specific redirected T cells. Malignant B cells appear to be an excellent target for redirected T cells, as B cells can serve as immunostimulatory antigen-presenting cells for T cells (Glimcher et al., 20, how. 155:445, 1982). IL-2 production by the CD20-specific scFvFc:ζ expressing Jurkat clones when co-cultured with CD20+ lymphoma did not require the addition of professional antigen presenting cells to culture or pharmacologic delivery of a co-stimulatory signal by the phorbal ester PMA. The capacity of B cell lymphoma cells to deliver co-stimulatory signals in our model system is supported by our observation that Jurkat cells express the CD28 receptor and B cell lymphoma lines used in this study are CD80-positive by flow cytometry (unpublished data). Immunohistochemical evaluation of lymphoma-containing lymph node specimens have detected CD80 expression by malignant B cells (Dorfman et al., *Blood* 90:4297, 1977). These observations support the rationale for using adoptive transfer of CD20-specific scFvFc:ζ-expressing CD4+ $T_{H1}$ cells in combination with CD8+ CTL based on their ability to produce IL-2 at sites of tumor where they can support the expansion of transferred CTL. CD28 signaling has recently been reported to inhibit activation-induced cell death of CTL when delivering a lytic event to tumor target cells and may contribute to the ease by which CTL are expanded in vitro and potentially in vivo when stimulated with transformed B cells such as LCL (Daniel et al., *J. Immunol.* 159:3808, 1997).

Lymphoma, by virtue of its lymph node tropism, is anatomically ideally situated for T cell-mediated recognition and elimination. The localization of infused T cells to lymph node in large numbers has been documented in HIV patients receiving infusions of HIV-specific CD8+ CTL clones. In these patients, evaluation of lymph node biopsy material revealed that infused clones constituted approximately 2–8% of CD8+ cells of lymph nodes [S. Riddell, personal communication]. Lymph node homing might be further improved by co-transfecting T cells with a cDNA construct encoding the L-selection molecule under a constitutive promoter since this adhesion molecule directs circulating T cells back to lymph nodes and is down-regulated by in vitro expansion (Chao et al., *J. Immunol.* 159:1686, 1997).

CD20 is an ideal target epitope for recognition by CD20-specific redirected T cells due to the prevalence of CD20+ disease, the uniformity of expression by tumor cells, and the stability of the CD20 molecule on the cell surface. This 33 kDa protein which is expressed on over 90% of B cell non-Hodgkins lymphoma, as well as normal mature B cells, but not hemapoietic stem cells or plasma cells, does not modulate or shed from the cell surface (Tedder et al., *Immunol. Today* 15:450, 1994. In addition to antitumor effector mechanisms intrinsic to T cells, it has been recently reported that CD20 crosslinking by soluble antibody can trigger apoptosis in selected B cell lymphoma lines (Shan et al., *Blood* 91:1664, 1998); such a killing mechanism may contribute to the biologic activity of CD20-specific scFvFc:ζ expressing T cells in vivo (Ghetie et al., *PNAS USA* 94:7509, 1997). Clinical trials evaluating the antitumor activity of chimeric anti-CD20 antibody IDEC-C2B8 (rituximab) in patients with relapsed low-grade non-Hodgkin's lymphoma have documented tumor responses in nearly half the patients treated and may reflect direct induction of apoptosis in vivo and/or the recruitment of antibody effector mechanisms via the human $IgG_1$ portion of the chimeric molecule (Maloney et al., *Blood* 90:2188, 1997). Radioimmunotherapy with $^{131}$I-conjugated and $^{90}$Y-conjugated anti-CD20 antibodies have demonstrated marked clinical efficacy in patients with relapsed/refractory non-Hodgkin's lymphoma, but toxicities have been significant (Eary et al., *Recent Result Cancer Res.* 141:177, 1996). The adoptive transfer of CD20-specific cytolytic T cells focuses an antigen-specific cellular immune response against lymphoma cells. The capacity of T cells to traffic to lymph nodes, lyse multiple targets, proliferate in response to antigenic stimulation, and persist in the tumor-bearing host for prolonged periods of time will overcome some of the limitations of soluble antibody therapy. CD20, however, is a self antigen and therefore subject to immune tolerance mechanisms preluding the generation of endogenous CD20-specific T cell responses. Engineering a CD20-specific cTCR is therefore an approach to re-direct T cell specificity to the CD20 molecule.

We have found that expansion of CD20 specific re-directed CD8+ CTL clones with OKT3 and IL-2 routinely results in the generation of greater than $10^9$ cells over period of approximately six weeks, and that the clones retain their effector function following expansion, as shown by functional chromium release assay data. Our observation that the plasmid/scFvFc:ζ system can generate transfectants with disrupted plasmid sequence underscores the desirability of cloning transfectants and expanding those clones demonstrating the presence of a single unrearranged integrated plasmid, expression of the chimeric receptor, and the capacity to specifically recognize and lyse CD20+ lymphoma target cells.

CD20 is not tumor-specific and adoptive transfer of cells with this specificity is expected to kill the subset of non-transformed B cells which express CD20. Although CD20 is not expressed by hematopoietic stem cells or mature plasma cells, this cross-reactivity may exacerbate the humoral immunodeficiency of patients receiving chemotherapy and/or radiotherapy. Equipping T cells with a suicide gene such as the herpes virus thymidine kinase gene allows for in vivo ablation of transferred cells following adoptive transfer with pharmacologic doses of gancyclovir and is a strategy for limiting the duration or in vivo persistence of transferred cells (Bonini et al., *Science* 276:1719, 1997).

CD20-specific chimeric receptor-expressing T cells of this invention can be used to treat patients with CD20⁺ Non-Hodgkin's lymphoma and CD20⁺ acute and chronic leukemias. High relapse rates observed following autologous transplantation for leukemia can be reduced with post-transplant in vivo treatment with adoptively transferred CD20-specific redirected T cells to purge CD20⁺ leukemic stem cells. CD20-specific redirected T cells can be used to treat lymphoma patients with refractory or recurrent disease. The CD20⁺ redirected T cells can be administered following myeloablative chemotherapy and stem cell rescue, when tumor burden and normal CD20⁺ cell burden are at a nadir and when the potential of an immunologic response directed against the scFvFc:ζ protein is minimized.

The anti-CD20 antibody IDEC-C2B8 (rituximab) is being used to treat a variety of autoimmune diseases as well as a method of immunosuppression prior to administering a foreign substance such as a monoclonal antibody or DNA or virus or cell in the situation where any immune response would decrease the effectiveness of the foreign agent. The CD20-specific chimeric receptor-expressing T cells of this invention can also be used for these purposes. Stated more generally, the CD20-specific chimeric receptor-expressing T cells of this invention can be used as a method to abrogate any untoward B cell function. These include antibody mediated autoimmune disease such as lupus and rheumatoid arthritis as well as any unwanted specific immune responses to a given antigen.

Patients can be treated by infusing therapeutically effective doses of CD8⁺ CD20-specific redirected T cells in the range of about $10^6$ to $10^{12}$ or more cells per square meter of body surface (cells/m²). The infusion will be repeated as often and as many times as the patient can tolerate until the desired response is achieved. The appropriate infusion dose and schedule will vary from patient to patient, but can be determined by the treating physician for a particular patient. Typically, initial doses of approximately $10^9$ cells/m² will be infused, escalating to $10^{10}$ or more cells/m². IL-2 can be co-administered to expand infused cells post-infusion. The amount of IL-2 can about $10^3$ to $10^6$ units per kilogram body weight. Alternatively or additionally, an scFvFc:ζ- expressing CD4⁺ $T_{H1}$ clone can be co-transferred to optimize the survival and in vivo expansion of transferred scFvFc:ζ- expressing CD8⁺ T cells. The dosing schedule may be based on Dr. Rosenberg's published work (Rosenberg et al., 1988 and 1993, supra) or an alternate continuous infusion strategy may be employed. CD20-specific redirected T cells can be administered as a strategy to support CD8⁺ cells as well as initiate/augment a Delayed Type Hypersensitivity response against CD20⁺ target cells.

What is claimed is:

1. A DNA construct encoding a CD20-specific chimeric T cell receptor wherein the receptor consists of an intracellular signaling domain selected from the group consisting of the human CD3 zeta chain, FcγRIII and FcεRI, a transmembrane domain and an extracellular domain, the extracellular domain comprising a CD20-specific receptor.

2. A plasmid expression vector containing a DNA construct of claim 1 in proper orientation for expression.

3. The DNA construct of claim 1 wherein the CD20-specific receptor comprises the Fv region of a single chain monoclonal antibody to CD20.

4. The DNA construct of claim 3 wherein the intracellular signaling domain is the intracellular signaling domain of the zeta chain of human CD3.

5. The DNA construct of claim 4 wherein the CD20-specific chimeric receptor comprises scFvFc:$\zeta$, wherein scFv designates the $V_H$ and $V_L$ chains of a single chain monoclonal antibody to CD20, Fc represents at least part of a constant region of an $IgG_1$, and $\zeta$ represents the intracellular signaling domain of the zeta chain of human CD3.

6. The DNA construct of claim 5 wherein the extracellular domain scFvFc and the intracellular signaling domain $\zeta$ are linked by the transmembrane domain of human CD4.

7. The DNA construct of claim 6 wherein the chimeric receptor is amino acids 21–633 of Seq. ID No. 2.

8. A plasmid expression vector containing the DNA construct of any of claims 3–7.

9. Genetically engineered CD20-specific T cells which express and bear on the cell surface membrane a CD20-specific chimeric receptor consisting of an intracellular signaling domain selected from the group consisting of the human CD3 zeta chain, Fc$\gamma$RIII and Fc$\epsilon$RI, a transmembrane domain and an extracellular domain, the extracellular domain comprising a CD20-specific receptor.

10. CD20-specific T cells of claim 9 which are non-malignant human cells.

11. CD20-specific T cells of claim 10 which are $CD4^{30}$ and which produce IL-2 when co-cultured in vitro with $CD20^+$ lymphoma cells.

12. CD20-specific T cells of claim 10 which are $CD8^+$ and which lyse $CD20^+$ lymphoma target cells when co-cultured in vitro with the target cells.

13. CD20-specific T cells of claim 10 which comprise a mixed population of $CD4^+$ and $CD8^+$ cells.

14. CD20-specific T cells of claim 10 wherein the CD20-specific receptor comprises the $V_H$ and $V_L$ chains of a single chain monoclonal antibody (scFv) to CD20.

15. CD20-specific T cells of claim 14 wherein the intracellular signaling domain is the intracellular signaling domain of the zeta chain of human CD3.

16. CD20-specific T cells of claim 15 wherein the CD20-specific chimeric receptor comprises scFvFc:$\zeta$, wherein scFv designates the $V_H$ and $V_L$ chains of a single chain monoclonal antibody to CD20, Fc represents at least part of a constant region of an $IgG_1$, and $\zeta$ represents the intracellular signaling domain of the zeta chain of human CD3.

17. CD20-specific T cells of claim 16 wherein the extracellular domain scFvFc and the intracellular signaling domain $\zeta$ are linked by the transmembrane domain of human CD4.

18. CD20-specific T cells of claim 17 wherein the chimeric receptor is amino acids 21–633 of Seq. ID No. 2.

19. A method of making and expanding the CD20-specific T cells of claim 9 which comprises transfecting T cells with an expression vector containing a DNA construct encoding the CD20-specific chimeric receptor, then stimulating the cells with $CD20^+$ cells, recombinant CD20, or an antibody to the receptor to cause the cells to proliferate.

20. The method of claim 19 wherein the transfected T-cells are cloned and a clone demonstrating presence of a single integrated unrearranged plasmid and expression of the chimeric receptor is expanded ex vivo.

21. The method of claim 20 wherein the clone selected for ex vivo expansion is $CD8^+$ and demonstrates the capacity to specifically recognize and lyse $CD20^+$ target cells.

22. The method of claim 21 wherein the chimeric receptor is amino acids 21–633 of Seq. ID No. 2.

* * * * *

UNITED STATES PATENT AND TRADEMARK OFFICE
CERTIFICATE OF CORRECTION

PATENT NO. : 6,410,319 B1
DATED : June 25, 2002
INVENTOR(S) : Raubitschek et al.

It is certified that error appears in the above-identified patent and that said Letters Patent is hereby corrected as shown below:

Column 8,
Line 65, "scFvFc:" should be -- scFvFc:3 --;

Column 16,
Line 60, "19989" should read as -- 1989 --.

Column 13,
Line 29, "CD4$^{30}$" should read as -- CD4$^+$ --.

Signed and Sealed this

Eighth Day of June, 2004

JON W. DUDAS
*Acting Director of the United States Patent and Trademark Office*

SEQUENCE LISTING

```
<160> NUMBER OF SEQ ID NOS: 14

<210> SEQ ID NO 1
<211> LENGTH: 1947
<212> TYPE: DNA
<213> ORGANISM: Artificial Sequence
<220> FEATURE:
<221> NAME/KEY: CDS
<222> LOCATION: (27)..(1925)
<220> FEATURE:
<223> OTHER INFORMATION: Description of Artificial  Sequence: Chimeric

<400> SEQUENCE: 1
ccagtgaatt ctcaggagcc gccacc atg gag aca gac aca ctc ctg cta tgg       53
                              Met Glu Thr Asp Thr Leu Leu Leu Trp
                               1               5 gtg ctg ctg ctc tgg gtt cca ggt tcc aca g gt gac att gtg ctg acc      101
Val Leu Leu Leu Trp Val Pro Gly Ser Thr G ly Asp Ile Val Leu Thr
 10                  15                  20                  25 caa tct cca gct atc ctg tct gca tct cca g gg gag aag gtc aca atg      149
Gln Ser Pro Ala Ile Leu Ser Ala Ser Pro G ly Glu Lys Val Thr Met
                 30                  35                  40 act tgc agg gcc agc tca agt gta aat tac a tg gac tgg tac cag aag      197
Thr Cys Arg Ala Ser Ser Ser Val Asn Tyr M et Asp Trp Tyr Gln Lys
             45                  50                  55 aag cca gga tcc tcc ccc aaa ccc tgg att t at gcc aca tcc aac ctg      245
Lys Pro Gly Ser Ser Pro Lys Pro Trp Ile T yr Ala Thr Ser Asn Leu
         60                  65                  70 gct tct gga gtc cct gct cgc ttc agt ggc a gt ggg tct ggg acc tct      293
Ala Ser Gly Val Pro Ala Arg Phe Ser Gly S er Gly Ser Gly Thr Ser
     75                  80                  85 tac tct ctc aca atc agc aga gtg gag gct g aa gat gct gcc act tat      341
Tyr Ser Leu Thr Ile Ser Arg Val Glu Ala G lu Asp Ala Ala Thr Tyr
 90                  95                 100                 105 tac tgc cag cag tgg agt ttt aat cca ccc a cg ttc gga ggg ggg acc      389
Tyr Cys Gln Gln Trp Ser Phe Asn Pro Pro T hr Phe Gly Gly Gly Thr
```

-continued

| | | | | | | | | | | | |
|---|---|---|---|---|---|---|---|---|---|---|---|
| | | 110 | | | 115 | | | 120 | | | |
| aag | ctg | gaa | ata | aaa | ggc | agt | act | agc | ggt | g gt | ggc tcc ggg ggc ggt | 437 |
| Lys | Leu | Glu | Ile | Lys | Gly | Ser | Thr | Ser | Gly | G ly | Gly Ser Gly Gly Gly |
| | | | 125 | | | 130 | | | | 135 | |

```
         110                    115                    120
aag ctg gaa ata aaa ggc agt act agc ggt g gt ggc tcc ggg ggc ggt    437
Lys Leu Glu Ile Lys Gly Ser Thr Ser Gly G ly Gly Ser Gly Gly Gly
            125                130                135 tcc ggt ggg ggc ggc agc agc gag gtg cag c tg cag cag tct ggg gct    485
Ser Gly Gly Gly Gly Ser Ser Glu Val Gln L eu Gln Gln Ser Gly Ala
        140                145                150 gag ctg gtg aag cct ggg gcc tca gtg aag a tg tcc tgc aag gct tct    533
Glu Leu Val Lys Pro Gly Ala Ser Val Lys M et Ser Cys Lys Ala Ser
    155                160                165 ggc tac aca ttt acc agt tac aat atg cac t gg gta aag cag aca cct    581
Gly Tyr Thr Phe Thr Ser Tyr Asn Met His T rp Val Lys Gln Thr Pro
170                175                180                185 gga cag ggc ctg gaa tgg att gga gct att t at cca gga aat ggt gat    629
Gly Gln Gly Leu Glu Trp Ile Gly Ala Ile T yr Pro Gly Asn Gly Asp
            190                195                200 act tcc tac aat cag aag ttc aaa ggc aag g cc aca ttg act gca gac    677
Thr Ser Tyr Asn Gln Lys Phe Lys Gly Lys A la Thr Leu Thr Ala Asp
        205                210                215 aaa tcc tcc agc aca gcc tac atg cag ctc a gc agc ctg aca tct gag    725
Lys Ser Ser Ser Thr Ala Tyr Met Gln Leu S er Ser Leu Thr Ser Glu
    220                225                230 gac tct gcg gac tat tac tgt gca aga tct a at tat tac ggt agt agc    773
Asp Ser Ala Asp Tyr Tyr Cys Ala Arg Ser A sn Tyr Tyr Gly Ser Ser
235                240                245 tac tgg ttc ttc gat gtc tgg ggc gca ggg a cc acg gtc acc gtc tcc    821
Tyr Trp Phe Phe Asp Val Trp Gly Ala Gly T hr Thr Val Thr Val Ser
250                255                260                265 tca ctc gac ccc aaa tct tct gac aaa act c ac aca tgc cca ccg tgc    869
Ser Leu Asp Pro Lys Ser Ser Asp Lys Thr H is Thr Cys Pro Pro Cys
        270                275                280 cca gca cct gaa ctc ctg ggg gga ccg tca g tc ttc ctc ttc ccc cca    917
Pro Ala Pro Glu Leu Leu Gly Gly Pro Ser V al Phe Leu Phe Pro Pro
    285                290                295 aaa ccc aag gac acc ctc atg atc tcc cgg a cc cct gag gtc aca tgc    965
Lys Pro Lys Asp Thr Leu Met Ile Ser Arg T hr Pro Glu Val Thr Cys
            300                305                310 gtg gtg gtg gac gtg agc cac gaa gac cct g ag gtc aag ttc aac tgg    1013
Val Val Val Asp Val Ser His Glu Asp Pro G lu Val Lys Phe Asn Trp
        315                320                325 tac gtg gac ggc gtg gag gtg cat aat gcc a ag aca aag ccg cgg gag    1061
Tyr Val Asp Gly Val Glu Val His Asn Ala L ys Thr Lys Pro Arg Glu
330                335                340                345 gag cag tac aac agc acg tac cgt gtg gtc a gc gtc ctc acc gtc ctg    1109
Glu Gln Tyr Asn Ser Thr Tyr Arg Val Val S er Val Leu Thr Val Leu
            350                355                360 cac cag gac tgg ctg aat ggc aag gag tac a ag tgc aag gtc tcc aac    1157
His Gln Asp Trp Leu Asn Gly Lys Glu Tyr L ys Cys Lys Val Ser Asn
        365                370                375 aaa gcc ctc cca gcc ccc atc gag aaa acc a tc tcc aaa gcc aaa ggg    1205
Lys Ala Leu Pro Ala Pro Ile Glu Lys Thr I le Ser Lys Ala Lys Gly
    380                385                390 cag ccc cga gaa cca cag gtg tac acc ctg c ca cca tca cga gat gag    1253
Gln Pro Arg Glu Pro Gln Val Tyr Thr Leu P ro Pro Ser Arg Asp Glu
    395                400                405 ctg acc aag aac cag gtc agc ctg acc tgc c tg gtc aaa ggc ttc tat    1301
Leu Thr Lys Asn Gln Val Ser Leu Thr Cys L eu Val Lys Gly Phe Tyr
410                415                420                425 ccc agc gac atc gcc gtg gag tgg gag agc a at ggg cag ccg gag aac    1349
```

```
Pro Ser Asp Ile Ala Val Glu Trp Glu Ser A sn Gly Gln Pro Glu Asn
              430                 435                 440 aac tac aag acc acg cct ccc gtg ctg gac t cc gac ggc tcc ttc ttc     1397
Asn Tyr Lys Thr Thr Pro Pro Val Leu Asp S er Asp Gly Ser Phe Phe
            445                 450                 455 ctc tac agc aag ctc acc gtg gac aag agc a gg tgg cag cag ggg aac     1445
Leu Tyr Ser Lys Leu Thr Val Asp Lys Ser A rg Trp Gln Gln Gly Asn
            460                 465                 470 gtc ttc tca tgc tcc gtg atg cat gag gct c tg cac aac cac tac acg     1493
Val Phe Ser Cys Ser Val Met His Glu Ala L eu His Asn His Tyr Thr
        475                 480                 485 cag aag agc ctc tcc ctg tct ccc ggg aaa a tg gcc ctg att gtg ctg     1541
Gln Lys Ser Leu Ser Leu Ser Pro Gly Lys M et Ala Leu Ile Val Leu
490                 495                 500                 505 ggg ggc gtc gcc ggc ctc ctg ctt ttc att g gg cta ggc atc ttc ttc     1589
Gly Gly Val Ala Gly Leu Leu Leu Phe Ile G ly Leu Gly Ile Phe Phe
                510                 515                 520 aga gtg aag ttc agc agg agc gca gac gcc c cc gcg tac cag cag ggc     1637
Arg Val Lys Phe Ser Arg Ser Ala Asp Ala P ro Ala Tyr Gln Gln Gly
            525                 530                 535 cag aac cag ctc tat aac gag ctc aat cta g ga cga aga gag gag tac     1685
Gln Asn Gln Leu Tyr Asn Glu Leu Asn Leu G ly Arg Arg Glu Glu Tyr
            540                 545                 550 gat gtt ttg gac aag aga cgt ggc cgg gac c ct gag atg ggg gga aag     1733
Asp Val Leu Asp Lys Arg Arg Gly Arg Asp P ro Glu Met Gly Gly Lys
        555                 560                 565 ccg aga agg aag aac cct cag gaa ggc ctg t ac aat gaa ctg cag aaa     1781
Pro Arg Arg Lys Asn Pro Gln Glu Gly Leu T yr Asn Glu Leu Gln Lys
570                 575                 580                 585 gat aag atg gcg gag gcc tac agt gag att g gg atg aaa ggc gag cgc     1829
Asp Lys Met Ala Glu Ala Tyr Ser Glu Ile G ly Met Lys Gly Glu Arg
                590                 595                 600 cgg agg ggc aag ggg cac gat ggc ctt tac c ag ggt ctc agt aca gcc     1877
Arg Arg Gly Lys Gly His Asp Gly Leu Tyr G ln Gly Leu Ser Thr Ala
            605                 610                 615 acc aag gac acc tac gac gcc ctt cac atg c ag gcc ctg ccc cct cgc     1925
Thr Lys Asp Thr Tyr Asp Ala Leu His Met G ln Ala Leu Pro Pro Arg
            620                 625                 630 taagcggccg cgaagcttcc gc                                             1947

<210> SEQ ID NO 2
<211> LENGTH: 633
<212> TYPE: PRT
<213> ORGANISM: Artificial Sequence
<220> FEATURE:
<223> OTHER INFORMATION: Description of Artificial  Sequence: Chimeric

<400> SEQUENCE: 2

Met Glu Thr Asp Thr Leu Leu Leu Trp Val L eu Leu Leu Trp Val Pro
  1               5                  10                  15

Gly Ser Thr Gly Asp Ile Val Leu Thr Gln S er Pro Ala Ile Leu Ser
                 20                  25                  30

Ala Ser Pro Gly Glu Lys Val Thr Met Thr C ys Arg Ala Ser Ser Ser
             35                  40                  45

Val Asn Tyr Met Asp Trp Tyr Gln Lys Lys P ro Gly Ser Ser Pro Lys
         50                  55                  60

Pro Trp Ile Tyr Ala Thr Ser Asn Leu Ala S er Gly Val Pro Ala Arg
 65                  70                  75                  80

Phe Ser Gly Ser Gly Ser Gly Thr Ser Tyr S er Leu Thr Ile Ser Arg
```

```
                     85                  90                  95
Val Glu Ala Glu Asp Ala Ala Thr Tyr Tyr Cys Gln Gln Trp Ser Phe
                100                 105                 110
Asn Pro Pro Thr Phe Gly Gly Gly Thr Lys Leu Glu Ile Lys Gly Ser
                115                 120                 125
Thr Ser Gly Gly Gly Ser Gly Gly Gly Ser Gly Gly Gly Gly Ser Ser
130                 135                 140
Glu Val Gln Leu Gln Gln Ser Gly Ala Glu Leu Val Lys Pro Gly Ala
145                 150                 155                 160
Ser Val Lys Met Ser Cys Lys Ala Ser Gly Tyr Thr Phe Thr Ser Tyr
                165                 170                 175
Asn Met His Trp Val Lys Gln Thr Pro Gly Gln Gly Leu Glu Trp Ile
                180                 185                 190
Gly Ala Ile Tyr Pro Gly Asn Gly Asp Thr Ser Tyr Asn Gln Lys Phe
                195                 200                 205
Lys Gly Lys Ala Thr Leu Thr Ala Asp Lys Ser Ser Ser Thr Ala Tyr
                210                 215                 220
Met Gln Leu Ser Ser Leu Thr Ser Glu Asp Ser Ala Asp Tyr Tyr Cys
225                 230                 235                 240
Ala Arg Ser Asn Tyr Tyr Gly Ser Ser Tyr Trp Phe Phe Asp Val Trp
                245                 250                 255
Gly Ala Gly Thr Thr Val Thr Val Ser Ser Leu Asp Pro Lys Ser Ser
                260                 265                 270
Asp Lys Thr His Thr Cys Pro Pro Cys Pro Ala Pro Glu Leu Leu Gly
                275                 280                 285
Gly Pro Ser Val Phe Leu Phe Pro Pro Lys Pro Lys Asp Thr Leu Met
                290                 295                 300
Ile Ser Arg Thr Pro Glu Val Thr Cys Val Val Val Asp Val Ser His
305                 310                 315                 320
Glu Asp Pro Glu Val Lys Phe Asn Trp Tyr Val Asp Gly Val Glu Val
                325                 330                 335
His Asn Ala Lys Thr Lys Pro Arg Glu Glu Gln Tyr Asn Ser Thr Tyr
                340                 345                 350
Arg Val Val Ser Val Leu Thr Val Leu His Gln Asp Trp Leu Asn Gly
                355                 360                 365
Lys Glu Tyr Lys Cys Lys Val Ser Asn Lys Ala Leu Pro Ala Pro Ile
                370                 375                 380
Glu Lys Thr Ile Ser Lys Ala Lys Gly Gln Pro Arg Glu Pro Gln Val
385                 390                 395                 400
Tyr Thr Leu Pro Pro Ser Arg Asp Glu Leu Thr Lys Asn Gln Val Ser
                405                 410                 415
Leu Thr Cys Leu Val Lys Gly Phe Tyr Pro Ser Asp Ile Ala Val Glu
                420                 425                 430
Trp Glu Ser Asn Gly Gln Pro Glu Asn Asn Tyr Lys Thr Thr Pro Pro
                435                 440                 445
Val Leu Asp Ser Asp Gly Ser Phe Phe Leu Tyr Ser Lys Leu Thr Val
                450                 455                 460
Asp Lys Ser Arg Trp Gln Gln Gly Asn Val Phe Ser Cys Ser Val Met
465                 470                 475                 480
His Glu Ala Leu His Asn His Tyr Thr Gln Lys Ser Leu Ser Leu Ser
                485                 490                 495
Pro Gly Lys Met Ala Leu Ile Val Leu Gly Gly Val Ala Gly Leu Leu
                500                 505                 510
```

```
Leu Phe Ile Gly Leu Gly Ile Phe Phe Arg Val Lys Phe Ser Arg Ser
        515                 520                 525

Ala Asp Ala Pro Ala Tyr Gln Gln Gly Gln Asn Gln Leu Tyr Asn Glu
        530                 535                 540

Leu Asn Leu Gly Arg Arg Glu Glu Tyr Asp Val Leu Asp Lys Arg Arg
545                 550                 555                 560

Gly Arg Asp Pro Glu Met Gly Gly Lys Pro Arg Arg Lys Asn Pro Gln
                565                 570                 575

Glu Gly Leu Tyr Asn Glu Leu Gln Lys Asp Lys Met Ala Glu Ala Tyr
        580                 585                 590

Ser Glu Ile Gly Met Lys Gly Glu Arg Arg Arg Gly Lys Gly His Asp
        595                 600                 605

Gly Leu Tyr Gln Gly Leu Ser Thr Ala Thr Lys Asp Thr Tyr Asp Ala
        610                 615                 620

Leu His Met Gln Ala Leu Pro Pro Arg
625                 630

<210> SEQ ID NO 3
<211> LENGTH: 32
<212> TYPE: DNA
<213> ORGANISM: Murine

<400> SEQUENCE: 3
ggtgatatcw tgmtgaccca awgtccactc tc                               32

<210> SEQ ID NO 4
<211> LENGTH: 32
<212> TYPE: DNA
<213> ORGANISM: Murine

<400> SEQUENCE: 4
ggtgatatcg tkctcacyca rtctccagca at                               32

<210> SEQ ID NO 5
<211> LENGTH: 36
<212> TYPE: DNA
<213> ORGANISM: Murine

<400> SEQUENCE: 5
gaggtgaagc tgcaggagtc aggacctagc ctggtg                           36

<210> SEQ ID NO 6
<211> LENGTH: 22
<212> TYPE: DNA
<213> ORGANISM: Murine

<400> SEQUENCE: 6
aggtsmagct gcagsagtcw gg                                          22

<210> SEQ ID NO 7
<211> LENGTH: 22
<212> TYPE: DNA
<213> ORGANISM: Murine

<400> SEQUENCE: 7
aggtscagct gcagsagtcw gg                                          22

<210> SEQ ID NO 8
<211> LENGTH: 26
<212> TYPE: DNA
```

```
<213> ORGANISM: Murine

<400> SEQUENCE: 8
cggaattcag gggccagtgg atagac                                                26

<210> SEQ ID NO 9
<211> LENGTH: 26
<212> TYPE: DNA
<213> ORGANISM: Murine

<400> SEQUENCE: 9
cggaattcgg atggtgggaa gatgga                                                26

<210> SEQ ID NO 10
<211> LENGTH: 18
<212> TYPE: PRT
<213> ORGANISM: Artificial Sequence
<220> FEATURE:
<223> OTHER INFORMATION: Description of Artificial  Sequence: J-Segment

<400> SEQUENCE: 10

Gly Ser Thr Ser Gly Gly Gly Ser Gly Gly G ly Ser Gly Gly Gly Gly
 1               5                  10                  15

Ser Ser

<210> SEQ ID NO 11
<211> LENGTH: 33
<212> TYPE: DNA
<213> ORGANISM: Homo sapiens

<400> SEQUENCE: 11
ggggaattcc ctcagcctct gcctcccagc ctc                                        33

<210> SEQ ID NO 12
<211> LENGTH: 33
<212> TYPE: DNA
<213> ORGANISM: Homo sapiens

<400> SEQUENCE: 12
ggggaattca tctgggcgtc tgcaggtctg gcc                                        33

<210> SEQ ID NO 13
<211> LENGTH: 20
<212> TYPE: DNA
<213> ORGANISM: Homo sapiens

<400> SEQUENCE: 13
ttcagcagga gcgcagcagc                                                       20

<210> SEQ ID NO 14
<211> LENGTH: 20
<212> TYPE: DNA
<213> ORGANISM: Homo sapiens

<400> SEQUENCE: 14
tagcgagggg gcagggcctg                                                       20
```